US009657305B2

(12) United States Patent
Paccalet et al.

(10) Patent No.: US 9,657,305 B2
(45) Date of Patent: May 23, 2017

(54) SYNTHESIS OF SIALIC ACID IN PLANTS

(71) Applicants: Medicago, Inc., Sainte-Foy, Quèbec (CA); Centre National de la Recherche Scientifique, Pars (FR); Universite De Rouen, Mont-Saint-Aignan (FR)

(72) Inventors: Thomas Paccalet, Rouen (FR); Muriel Bardor, Mont Saint Aignan (FR); Christophe Rihouey, Sainte-Foy (CA); Véronique Gomord, Rouen (FR); Loïc Faye, Saint-Jacques-sur-Darnétal (FR); Patrice Lerouge, Grand Couronne (FR); Stéphanie Aquin, Chavannes (CH); Louis-Philippe Vezina, Neuville (CA); Marc-André D'Aoust, Québec (CA)

(73) Assignees: Medicago Inc., Quebec (CA); Centre National de la Recherche Scientifique, Paris (FR); Universite De Rouen, Mont-Saint-Aignan (FR)

(*) Notice: Subject to any disclaimer, the term of this patent is extended or adjusted under 35 U.S.C. 154(b) by 0 days.

(21) Appl. No.: 14/932,326

(22) Filed: Nov. 4, 2015

(65) Prior Publication Data
US 2016/0145664 A1 May 26, 2016

Related U.S. Application Data

(62) Division of application No. 12/278,677, filed as application No. PCT/CA2007/000197 on Feb. 9, 2007, now Pat. No. 9,212,372.

(60) Provisional application No. 60/743,267, filed on Feb. 9, 2006.

(51) Int. Cl.
*C12N 15/82* (2006.01)
*C12N 9/88* (2006.01)
*C12P 19/26* (2006.01)
*C12P 21/00* (2006.01)

(52) U.S. Cl.
CPC .......... *C12N 15/8257* (2013.01); *C12N 9/88* (2013.01); *C12N 15/8245* (2013.01); *C12P 19/26* (2013.01); *C12P 21/005* (2013.01)

(58) Field of Classification Search
None
See application file for complete search history.

(56) References Cited

U.S. PATENT DOCUMENTS

| 5,233,033 | A  | 8/1993  | Koketsu et al.    |
| 6,846,656 | B1 | 1/2005  | Koizumi et al.    |
| 6,949,372 | B2 | 9/2005  | Betenbaugh et al. |
| 7,741,539 | B2 | 6/2010  | Gorr et al.       |
| 8,907,163 | B2 | 12/2014 | Bakker et al.     |
| 2002/0142386 | A1 | 10/2002 | Betenbaugh et al. |
| 2012/0237972 | A1 | 9/2012  | Bakker et al.     |

FOREIGN PATENT DOCUMENTS

| EP | 0 578 825 A1   | 1/1994  |
| EP | 1 541 693 A1   | 6/2005  |
| JP | 2001-136982 A  | 5/2001  |
| WO | WO 00/56906 A1 | 9/2000  |
| WO | WO 01/31045 A1 | 5/2001  |
| WO | WO 02/33070 A1 | 4/2002  |
| WO | WO 02/36786 A2 | 5/2002  |
| WO | WO 03/072783 A1 | 9/2003 |
| WO | WO 03/078637 A2 | 9/2003 |
| WO | WO 2004/063370 A1 | 7/2004 |
| WO | WO 2004/071177 A2 | 8/2004 |
| WO | WO 2005/090552 A2 | 9/2005 |
| WO | WO 2007/006570 A2 | 1/2007 |
| WO | WO 2007/016276 A2 | 2/2007 |
| WO | WO 2008/151444 A1 | 12/2008 |

OTHER PUBLICATIONS

Ferrero et al. N-Acetyl-D-neuraminic acid lyase generates the sialic acid for colominic acid biosynthesis in *Escherichia coli* K1. (1996) Biochem. J.; vol. 317; pp. 157-165.*
Gomord et al. Production and glycosylation of plant-made pharmaceuticals: the antibodies as a challenge. (2004) Plant Biotech. J.; vol. 2; pp. 83-100.*
Angata, T., et al., "Chemical diversity in the sialic acids and related α-keto acids: An evolutionary perspective," *Chem. Rev.* 102(2): 439-469, American Chemical Society, Washington, DC (Feb. 2002).
Aumiller, J.J., et al., "A transgenic insect cell line engineered to produce CMP-sialic acid and sialylated glycoproteins," *Glycobiology* 13(6): 497-507, IRL Press at Oxford University Press, Oxford, UK (Jun. 2003).
Bakker, H., et al., "Galactose-extended glycans of antibodies produced by transgenic plants," *Proc. Natl. Acad. Sci. USA* 98(5): 2899-2904, National Academy of Sciences, Washington, DC (Feb. 2001).
Bardor, M., et al., "Immunoreactivity in mammals of two typical glyco-epitopes, core α(1,3)-fucose and core xylose," *Glycobiology* 13(6): 427-434, IRL Press at Oxford University Press, England (Jun. 2003; E-pub. Dec. 2002).

(Continued)

*Primary Examiner* — Cathy Kingdon Worley
(74) *Attorney, Agent, or Firm* — Sterne, Kessler, Goldstein & Fox P.L.L.C.

(57) ABSTRACT

A method of synthesizing sialic acid in plants, and plants capable of synthesizing sialic acid is provided. Furthermore, a method of producing sialylated protein in a plant is also provided. The method to synthesize sialic acid comprises providing a plant comprising a nucleotide sequence encoding N-acetyl neuraminic acid (Neu5Ac) synthase or Neu5Ac lyase, and expressing the nucleotide sequence thereby synthesizing sialic acid. The plant may also co-express a nucleotide sequence encoding one or more than one of an epimerase, a CMP-Neu5Ac synthase, a CMP-Neu5Ac transporter and a sialyltransferase.

3 Claims, 3 Drawing Sheets

(56) References Cited

OTHER PUBLICATIONS

European Search Report (Supplementary) for the corresponding EP Application No. EP 07 71 0612, The Hague, Netherlands, search completed on Aug. 4, 2009.

Ferrero, M.A., et al., "N-Acetyl-D-neuraminic acid lyase generates the sialic acid for colominic acid biosynthesis in *Escherichia coli* K1," *Biochem. J.* 317(Pt. 1): 157-165, Published by Portland Press on behalf of the Biochemical Society, London, England (Jul. 1996).

Giritch, A., et al., "Rapid high-yield expression of full-size IgG antibodies in plants coinfected with non-completing viral vectors," *Proc. Natl. Acad. Sci. USA* 103(40): 14701-14706, National Academy of Sciences, Washington, DC (Oct. 2006; E-pub. Sep. 2006).

Gomord, V., et al., "Production and glycosylation of plant-made pharmaceuticals: the antibodies as a challenge," *Plant Biotechnology Journal* 2(2): 83-100, Blackwell-Wiley, Hoboken, NJ (Mar. 2004).

International Search Report (mailed May 22, 2007); Written Opinion (mailed May 22, 2007), Chapter II International Preliminary Report on Patentability Completed Jun. 9, 2008) and annexes thereto; for the corresponding International Application No. PCT/CA2007/000197, filed Feb. 7, 2007, Canadian Intellectual Property Office, Quebec, Canada.

International Search Report (mailed Sep. 12, 2008); Written Opinion (Sep. 12, 2008), Chapter II International Preliminary Report on Patentability Completed Oct. 16, 2009) and annexes thereto; for related International Application No. PCT/CA2008/001146, filed Jun. 18, 2008, Canadian Intellectual Property Office, Quebec, Canada.

Johansen, L.K., et al., "Silencing on the Spot. Induction and Suppression of RNA Silencing in the *Agrobacterium*-Mediated Transient Expression System," *Plant Physiology* 126(3): 930-938, American Society of Plant Physiologists, Rockville, MD (Jul. 2001).

Joshi, L. et al., "Bioprospecting in plants for engineered proteins," *Current Opinions in Plant Biology* 8(2): 223-226, Academic Press, New York, NY (Apr. 2005).

Kelm, S., et al., "Sialic acids in molecular and cellular interactions," *Int. Rev. Cytol.* 175: 137-240, Academic Press, New York, NY (1997).

Kim, K., et al., "Expression of a functional *Drosophila melanogaster* N-acetylneuraminic acid (Neu5Ac) phosphate synthase gene: evidence for endogenous sialic acid biosynthetic ability in insects," *Glycobiology* 12(2): 73-83, IRL Press at Oxford University Press, Oxford, UK (Feb. 2002).

Ko, K., et al., "Function and glycosylation of plant-derived antiviral monoclonal antibody," *Proc. Natl. Acad. Sci. USA*, 100(13): 8013-8018, National Academy of Sciences, Washington, DC (Jun. 2003).

Lawrence S.M., et al., "Cloning and expression of the human N-acetylneuraminic acid phosphate synthase gene with 2-keto-3-deoxy-D-*glycero*-D-*galacto*-nononic acid biosynthetic ability," *J. Biol. Chem.* 275(23): 17869-17877, American Society for Biochemistry and Molecular Biology, Rockville, MD (Jun. 2000).

Lawrence, S.M., et al., "Cloning and expression of human sialic acid pathway genes to generate CMP-sialic acids in insect cells," *Glycoconjugate Journal* 18(3): 205-213, Kluwer Academie Publishers, The Netherlands (Mar. 2001).

Lerouge, P., "N-Glycoprotein biosynthesis in plants: recent developments and future trends," *Plant Mol. Biol.* 38(1-2): 31-48, Kluwer Academic, The Netherlands (Sep. 1998).

Maru, I., et al., "Simple and large-scale production of N-acetylneuraminic acid from N-acetyl-D-glucosamine and pyruvate using N-acyl-D-glucosamine 2-epimerase and N-acetylneuraminate lyase," *Carbohydr. Res.* 306(4): 575-578, Elsevier, The Netherlands (Feb. 1998).

Matsumoto, S., et al., "Characterization of human glycoprotein (erythropoietin) produced in cultured tobacco cells," *Plant Mol. Biol.* 27(6): 1163-1172, Kluwer Academic, Netherlands (Mar. 1995).

Misaki, R., et al., "Expression of human CMP-N-acetylneuraminic acid synthetase and CMP-sialic acid transporter in tobacco suspension-cultured cell," *Biochem Biophys Res Commun* 339(4): 1184-1189, Academic Press, New York, NY (Jan. 2006; E-pub. Dec. 2005).

Paccalet, T., et al., "Engineering of a sialic acid synthesis pathway in transgenic plants by expression of bacterial Neu5Ac-synthesizing enzymes," *Plant Biotechnology Journal* 5(1): 16-25, Blackwell-Wiley, Hoboken, NJ (Jan. 2007).

Pagny, S., "Protein recycling from the Golgi apparatus to the endoplasmic reticulum in plants and its minor contribution to calreticulin retention," *Plant Cell* 12(5): 739-755, American Society of Plant Physiologists, Rockville, MD (May 2000).

Palacpac, N.Q., et al., "Stable expression of human β1,4-galactosyltransferase in plant cells modifies N-linked glycosylation patterns," *Proc. Natl. Acad. Sci. USA*, 96(8): 4692-4697, National Academy of Sciences, Washington, DC (Apr. 1999).

Reaves, M.L. et. al., "Expression of human N-acetylneuraminic acid phosphate synthase and bacterial N-acetyl neuraminc acid synthase in tobacco plants," *The 19th Rocky Mountain Regional Meeting*, Abstract 42, Tuscon, AZ (Oct. 14-18, 2006).

Séveno, M., et al., "Glycoprotein sialylation in plants?," *Nature Biotechnology* 22(11): 1351-1352, Nature Publishing Group, New York, NY (Nov. 2004).

Shah M, et al., "Sialyted endogenous glycoconjugates in plant cells," *Nature Biotechnology* 21(12): 1470-1471, Nature Publishing Group, New York, NY(Dec. 2003).

Spokevicius, A.V., et al., "*Agrobacterium*-mediated transformation of dormant lateral buds in poplar trees reveals developmental patterns in secondary stem tissues," *Functional Plant Biology* 33(2): 133-139, CSIRO Publishing, Collingwood, VIC, Australia (Feb. 2006).

Sriraman, R., et al., "Recombinant anti-hCG antibodies retained in the endoplasmic reticulum of transformed plants lack core-xylose and core α(1,3)-fucose residues," *Plant Biotech. J.* 2(4): 279-287, Blackwell-Wiley, Hoboken, NJ (Jul. 2004).

Sundaram, A., et al., "Characterization of N-acetylneuraminic acid synthase isoenzyme 1 from *Campylobacter jejuni*," *Biochem. J.* 383(Pt. 1): 83-89, Published by Portland Press on behalf of the Biochemical Society, London, England (Oct. 2004).

Tanner, M.E., "The enzymes of sialic acid biosynthesis," *Bioorg. Chem.*, 33(3): 216-228, Academic Press, New York, NY (Jun. 2005).

Traving, C., et al., "Structure, function and metabolism of sialic acids," *Cell. Mol. Life Sci.* 54(12): 1330-1349, Birkhäuser, Switzerland (Dec. 1998).

Triguero A., et al., "Plant-derived mouse IgG monoclonal antibody fused to KDEL endoplasmic reticulum-retention signal is N-glycosylated homogeneously throughout the plant with mostly high-mannose type N-glycans," *Plant Biotech J.* 3(4): 449-457, Blackwell-Wiley, Hoboken, NJ (Jul. 2005).

Viswanathan, K., et al., "Engineering sialic acid synthetic ability into insect cells: identifying metabolic bottlenecks and devising strategies to overcome them," *Biochemistry* 42(51): 15215-15225, American Chemical Society, Washington, DC (Dec. 2003).

Wee, E.G.-T., et al., "Targeting of active sialyltransferase to the plant Golgi apparatus." *Plant Cell*, 10(10): 1759-1768, American Society of Plant Physiologists, Rockville, MD (Oct. 1998).

Communication pursuant to Article 94(3) EPC for EP 07 710 612.8-1212, mailed Dec. 2, 2009.

Examination Report for NZ Patent Application No. 570455, dated May 24, 2010, Intellectual Property Office of New Zealand, Wellington, NZ.

Extended European search report for EPO Patent Application No. 10166705.3, dated Jul. 14, 2010, European Patent Office, Rijswijk, Netherlands.

Gomord, V. et al., "Biopharmaceutical production in plants: problems, solutions and opportunities," *TRENDS in Biotech.* 23:561-565 (Nov. 2005), Elsevier Ltd.

"Communication pursuant to Article 94(3) EPC" dated Apr. 22, 2010, for corresponding European Patent Application No. 07 710 612.8, The European Patent Office, Rijswijk, Netherlands, (4 pages).

(56) References Cited

OTHER PUBLICATIONS

"Decision to grant a European patent pursuant to Article 97(1) EPC" dated May 26, 2011, for corresponding European Patent Application No. 07 710 612.8, The European Patent Office, Rijswijk, Netherlands, (2 pages).
English translation of "Text of the First Office Action" dated Jun. 18, 2010, for corresponding Chinese Patent Application No. 200780011193.9, State Intellectual Property Office of the People's Republic of China, Beijing, China, (2 pages).
English translation of "Notice of Grant of Patent Right for Invention" dated Dec. 19, 2011, for corresponding Chinese Patent Application No. 200780011193.9, State Intellectual Property Office of the People's Republic of China, Beijing, China, (6 pages).
English translation of "Notification of Defects in Patent Application No. 193333" dated Sep. 7, 2010, for corresponding Israeli Patent Application No. 193333, Israel Patent Office, Jerusalem, Israel, (3 pages).
English translation of "Notification of Defects in Patent Application No. 193333" dated Apr. 28, 2011, for conesponding Israeli Patent Application No. 193333, Israel Patent Office, Jerusalem, Israel, (2 pages).
"Examination Report" dated Nov. 24, 2011, for corresponding New Zealand Patent Application No. 596626, New Zealand Intellectual Property Office, (2 pages).
Linton, D., et al., "Multiple N-acetyl neuraminic acid synthetase (neuB) genes in Campylobacter jejuni: identification and characterization of the gene involved in sialylationof lipo-oligosaccharide," Molcular Microbiology 35(5):1120-1134, Blackwell Science Ltd., England (2000).
Liu, J., et al., "Overproduction of CMP-Sialic Acid Synthetase for Organic Synthesis," J. Am Chem. Soc. 114:3901-3910, American Chemical Society, United States (1992).
Ohta, Y., et al.,"Complete Nucleotide Sequence of the E. coli N-acetylneuraminate lyase," Nucleic Acids Research 13(24):8843-8862, IRL Press Limited, England (1985).
Office Action in corresponding Canadian Application CA 2,649,134, dated Jul. 23, 2012, Canadian Intellectual Property Office, Canada, 4 pages.
Office Action with English language Translation in corresponding Japanese Application 2008-553589, dated Sep. 19, 2012, Japanese Patent Office, Japan, 9 pages.
"Examination Report" dated Mar. 13, 2012, for corresponding Australian Patent Application No. 2007214227, Australian Intellectual Property Office, Australia, 2 pages.
"Notice of Acceptance" dated Sep. 12, 2012, for corresponding Australian Patent Application No. 2007214227, Australian Intellectual Property Office, 4 pages.
"Decision to Grant a European patent pursuant to Article 97(1) EPC" dated Oct. 5, 2010, for corresponding European Patent Application No. 10166705.3, European Patent Office, Rijswijk, Netherlands, 2 pages.
"Certificate of Patent" with claims allowed, dated Sep. 1, 2012, for corresponding Israeli Patent No. 193333, State of Israel Patent Office, Israel, 8 pages "Letters Patent" with claims allowed, dated Apr. 2, 2012, for corresponding New Zealand Patent No. 570455, New Zealand Intellectual Property Office, New Zealand, 7 pages.
"Notice of Allowance" dated Feb. 25, 2013, for corresponding Canadian Patent Application No. 2,649,134, Canadian Intellectual Property Office, Canada, 1 page.
Office Action with English language Translation in corresponding Chinese Application No. 2012100273796, dated Jan. 29, 2013, State Intellectual Property Office of the People's Republic of China, China, 9 pages.
Liu, Z., et al., "Enzyme from Higher Eukaryotes for Industrial Biocatalysis," Food Technol. Biotechnol. 42(4): 237-249, Sveučilište u Zagrebu, Croatia (2004).
Office Action issued Sep. 18, 2013, in corresponding Indian Application No. 7569/DELNP/2008, Government of India Patent Office Intellectual Property Building, 2 pages.
Office Action issued Sep. 16, 2013, in corresponding Chinese Application No. 201210027379.6, State Intellectual Property Office of the People's Republic of China, 12 pages.
Lewis, A.L., et al. "Discovery and characterization of sailic acid O-acetylation in group B Streptococcus," Proc. Nat. Acad. Sci. 101(30):11123-11128, National Academy of Sciences, United States (2004).
Mizanur, R.M. and Pohl, N.L., "Bacterial CMP-sialic acid synthetases: production, properties, and applications," Appl Microbiol Biotechnol 80:757-765, Springer-Verlag, Germany (2008).
Rishi, A.S., et al., "Molecular Farming in Plants: A Current Prospective," J Plan Biochemistry & Biotechnology 10:01-12 (2001).
Warner, T.G., "Metabolic Engineering Glycosylation Biotechnology's Challenge to the Glycobiologist in the Next Millennium," in Carbohydrates in Chemistry and Biology, eds. Ernst, Hart, and Sanay, pp. 1043-1064, Wiley-Vch, United States (2000).
Notice of Allowance in corresponding Canadian Application CA 2,813,435, dated Jan. 20, 2014, Canadian Intellectual Property Office, Canada, 1 page.
English translation of "Text of the Decision on Rejection" dated Mar. 31, 2014, for corresponding Chinese Patent Application No. 201210027379.6, State Intellectual Property Office of the People's Republic of China, Beijing, China, 6 pages.
English translation of "Text of the Reexamination Notification" dated Jan. 7, 2016, for corresponding Chinese Patent Application No. 201210027379.6, State Intellectual Property Office of the People's Republic of China, Beijing, China, 5 pages.
"Certificate of Patent" dated Mar. 20, 2014, for corresponding Japanese Patent No. 5502328 (Japanese Application 2008-553589), Japanese Patent Office, Japan, 3 pages.
Final Office Action with English language Translation in corresponding Japanese Application 2008-553589, dated Aug. 15, 2013, Japanese Patent Office, Japan, 8 pages.
"Certificate of Patent" dated Apr. 8, 2014, for corresponding Korean Patent No. 10-1385051 (Korean Application 2008-7022025), Korean Patent Office, Korea, 4 pages.

* cited by examiner

SYNTHESIS OF SIALIC ACID IN PLANTS

FIELD OF INVENTION

The present invention relates to the synthesis of sialic acid in plants. Furthermore the present invention provides methods and plants that produce sialic acid, and sialylated proteins produced from these plants.

BACKGROUND OF THE INVENTION

Plants are potentially a low cost and contamination safe factory for the production of recombinant pharmaceutical proteins. Most of the recombinant proteins produced in plants are indistinguishable from their mammalian counterparts, as far as the amino acid sequence, conformation and biological activity. Furthermore, mammalian glycoproteins are efficiently glycosylated when they are expressed in transgenic plants. However, plants produce molecules with N-glycans that differ from those found on animal glycoproteins (Lerouge et al., 1998). This may limit the use of plant-made pharmaceuticals since the presence of plant-specific glyco-epitopes on these proteins may elicit immune responses in humans (Bardor et al., 2003) as well as the absence of mammalian-type epitopes, such as sialylated sequences, may induce their fast clearance from the blood stream. As a consequence, controlling the N-glycosylation of plant-made pharmaceuticals is a prerequisite for their use in human therapy.

In planta remodelling strategies have recently emerged to obtain plant-derived antibodies with human compatible carbohydrate profiles. Some strategies involved the retention of the plantibodies in the endoplasmic reticulum (Ko et al., 2003; Sriraman et al., 2004, Triguero et al., 2005), others involved the transformation of plants with mammalian glycosyltransferases. For example, plant N-glycosylation can be partially humanised by transformation of plant with a human β(1,4)-galactosyltransferase (Palacpac et al., 1999; Bakker et al., 2001). Expression of a murine antibody in a transformed plant resulted in the production of a plant-derived antibody harbouring a galactosylation profile similar to the one observed in the corresponding murine IgG (Bakker et al., 2001).

Mammalian IgGs bear bi-antennary N-glycans on the conserved site of N-glycosylation located in the Fc domain. These oligosaccharides are weakly sialylated, and the absence of terminal Neu5Ac does not interfere with the antibody function and stability. In contrast, most other circulatory glycoproteins have sialylated di-, tri or tetra antennary N-glycans. The presence of terminal sialic acids on these glycans is required for numerous biological functions, the first one being the control of the half-life of the protein in the circulatory system. In the absence of terminal sialic acids, glycoproteins are detected by hepatic asialoglycoprotein receptors and cleared from the serum, rendering these proteins biologically short-lived and ineffective (Kelm and Schauer, 1997). Therefore, non-sialylated plant-made pharmaceuticals may be rapidly eliminated from the blood stream when injected to a human, for example, a tobacco-derived Epo was biologically active in vitro but non functional in vivo because of its removal from the circulation before it reached erythropoietic tissues (Matsumoto et al., 1995).

Remodeling of N-glycans linked to plantibodies into human-like N-glycans has been already partially achieved in plants by expression of a human β(1,4)-galactosyltransferase (Palacpac et al., 1999; Bakker et al., 2001), a transferase that uses the endogenous UDP-Gal as co-substrate. A mammalian sialyltransferase has also been introduced in plants and demonstrated to be functional and correctly targeted to the Golgi apparatus (Wee et al., 1998). However, no sialylation of endogenous oligosaccharides was observed. The occurrence of sialic acids as well as the sialylation machinery in plants is still a matter of debate. However, Neu5Ac, the major sialic acid present in humans, as well as its precursor N-acetylmannosamine (D-ManNAc) do not appear to be synthesised in plants in detectable amounts (Séveno et al., 2004). As a consequence, the glyco-engineering of plant N-glycans into sialylated oligosaccharides requires the co-expression of exogenous enzymes able to catalyse the synthesis, the activation and the transfer in the Golgi apparatus of Neu5Ac.

In mammals and bacteria, anabolism and catabolism of Neu5Ac occurs through different pathways (Angata and Varki, 2002). Two main classes of enzymes are required to form Neu5Ac. N-acetylneuraminate lyases (Neu5Ac lyase) is involved in the catabolism of sialic acids by catalysing the cleavage of Neu5Ac into N-acetylmannosamine (D-ManNAc) and pyruvate in a reversible reaction. At high concentrations of D-ManNAc and pyruvate, the equilibrium can be shifted to the synthesis of Neu5Ac. Coupled to a glucosamine 2-epimerase activity, Neu5Ac lyase from *E. coli* was used for the large-scale production of Neu5Ac from D-GlcNAc (Maru et al., 1998). Alternatively, Neu5Ac synthases, such as NeuB, catalyze the condensation of ManNAc onto phosphoenol pyruvate (PEP) and are directly involved in the biosynthesis of sialic acids (reviewed in Tanner, 2005).

SUMMARY OF THE INVENTION

The present invention relates to the synthesis of sialic acid in plants. Furthermore the present invention provides methods and plants that produce sialic acid, and sialylated proteins produced from these plants.

It is an object of the invention to provide an improved method of producing sialic acid in a plant.

According to the present invention there is provided method (A) of synthesizing sialic acid, for example N-acetyl neuraminic acid (Neu5Ac), comprising, i) providing a plant comprising a nucleotide sequence encoding Neu5Ac synthase or Neu5Ac lyase, the nucleotide sequence operatively linked with a regulatory region that is active in the plant, and ii) growing the plant and expressing the nucleotide sequence thereby synthesizing the sialic acid.

Furthermore, after the step of growing, the sialic acid may be recovered from the plant. The regulatory region may be selected from the group consisting of a constitutive promoter, an inducible promoter, a tissue specific promoter, and a developmental promoter.

The present invention also pertains to the method defined above (Method A), wherein in the step of providing, the plant further comprises a second nucleotide sequence encoding one or more than one of an epimerase, a CMP-Neu5Ac synthase, a CMP-Neu5Ac transporter, a galactosyltransferase, and a sialyltransferase, operatively linked to one or more than one second regulatory region active within the plant, and the second nucleotide sequence is co-expressed along with the expression of the nucleotide sequence. Furthermore, the second regulatory region may be selected from the group consisting of a constitutive promoter, an inducible promoter, a tissue specific promoter, and a developmental promoter.

The present invention also pertains to the method as described above (Method A), wherein the nucleotide sequence encoding Neu5Ac synthase or Neu5Ac lyase, the second nucleotide sequence encoding one or more than one of the epimerase, CMP-Neu5Ac synthase, or CMP-Neu5Ac transporter, or both the nucleotide sequence, and the second nucleotide sequence is codon optimized for expression within the plant.

The present invention provides a method (B) of producing a protein of interest comprising, i) providing a plant that expresses one or more than one first nucleotide sequence encoding Neu5Ac synthase, Neu5Ac lyase, an epimerase, a CMP-Neu5Ac synthase, a CMP-Neu5Ac transporter, a galactosyltransferase, and a sialyltransferase, and a second nucleotide sequence encoding the protein of interest, ii) growing the plant and expressing the first and second nucleotide sequences thereby producing the protein of interest, wherein the protein of interest is sialylated.

Preferably, the protein of interest that is sialylated comprises di, tri or tetra antennary N-glycans.

The present invention also pertains to the method as defined above (Method B) wherein the sialylated protein is extracted from the plant. Furthermore, the sialylated protein may be isolated and purified.

The present invention provides a plant, a plant cell, or a seed, comprising a nucleotide sequence encoding Neu5Ac synthase or Neu5Ac lyase operatively linked with a regulatory region that is active in the plant. The plant, the plant cell or the seed may further comprise a second nucleotide sequence encoding one or more than one of an epimerase, a CMP-Neu5Ac synthase, a CMP-Neu5Ac transporter, a galactosyltransferase, and a sialyltransferase, operatively linked to one or more than one second regulatory region active within the plant. Furthermore, the regulatory region and the second regulatory regions may be selected from the group consisting of a constitutive promoter, an inducible promoter, a tissue specific promoter, and a developmental promoter.

The present invention pertains to the method as described above (Method B), wherein the one or more than one first nucleotide sequence encoding Neu5Ac synthase, Neu5Ac lyase, an epimerase, a CMP-Neu5Ac synthase, a CMP-Neu5Ac transporter, a galactosyltransferase, a sialyltransferase, a second nucleotide sequence encoding the protein of interest, or both the first nucleotide sequence, and the second nucleotide sequence is codon optimized for expression within the plant, plant cell, or the seed.

The present invention includes a plant, a plant cell, or a seed, comprising a nucleotide sequence encoding Neu5Ac synthase or Neu5Ac lyase operatively linked with a regulatory region that is active in the plant. The plant, the plant cell or the seed may further comprising a second nucleotide sequence encoding one or more than one of an epimerase, a CMP-Neu5Ac synthase, a CMP-Neu5Ac transporter, a galactosyltransferase, and a sialyltransferase, operatively linked to one or more than one second regulatory region active within the plant. Furthermore, the nucleotide sequence encoding Neu5Ac synthase or Neu5Ac lyase, the second nucleotide sequence encoding one or more than one of the epimerase, CMP-Neu5Ac synthase, or CMP-Neu5Ac transporter, or both the nucleotide sequence, and the second nucleotide sequence is codon optimized for expression within the plant, plant cell, or the seed.

The present invention also provides to a plant, a plant cell, or a seed, comprising one or more than one first nucleotide sequence encoding Neu5Ac synthase, Neu5Ac lyase, an epimerase, a CMP-Neu5Ac synthase, a CMP-Neu5Ac transporter, a galactosyltransferase, and a sialyltransferase, and a second nucleotide sequence encoding a protein of interest, the first and second nucleotide sequence operatively linked with one or more than one regulatory region that is active in the plant. The one or more than one regulatory region may be selected from the group consisting of a constitutive promoter, an inducible promoter, a tissue specific promoter, and a developmental promoter. Furthermore, the one or more than one first nucleotide sequence encoding Neu5Ac synthase, Neu5Ac lyase, an epimerase, a CMP-Neu5Ac synthase, a CMP-Neu5Ac transporter, a galactosyltransferase, a sialyltransferase, a second nucleotide sequence encoding the protein of interest, or both the first nucleotide sequence, and the second nucleotide sequence is codon optimized for expression within the plant, plant cell, or the seed.

The present invention also provides a method (Method C) of synthesizing sialic acid comprising, transiently transforming a plant, or a portion of the plant with a nucleotide sequence encoding N-acetyl neuraminic acid (Neu5Ac) synthase or Neu5Ac lyase, the nucleotide sequence operatively linked with a regulatory region that is active in the plant, and expressing the nucleotide sequence thereby synthesizing sialic acid. Furthermore, the Neu5Ac or the Neu5Ac lyase may be recovered from the plant or a portion of the plant.

The present invention also pertains to the method as described above (Method C), wherein in the step of transiently transforming the plant or a portion of the plant, further comprises a second nucleotide sequence encoding one or more than one of an epimerase, a CMP-Neu5Ac synthase, or a CMP-Neu5Ac transporter, operatively linked to one or more than one second regulatory region active within the plant, and the second nucleotide sequence is co-expressed along with the expression of the nucleotide sequence.

The present invention provides a method (method D) of producing a protein of interest comprising, i) transiently transforming a plant or portion of the plant with a construct that expresses one or more than one first nucleotide sequence encoding Neu5Ac synthase, Neu5Ac lyase, an epimerase, a CMP-Neu5Ac synthase, a CMP-Neu5Ac transporter, a galactosyltransferase, a sialyltransferase, and a second nucleotide sequence encoding the protein of interest, and ii) producing the protein of interest, wherein the protein of interest is sialylated.

The protein of interest that is sialylated may comprise di, tri or tetra antennary N-glycans. Furthermore, the sialylated protein may extracted from the plant or portion of the plant. The sialylated protein of interest may also be isolated and purified.

The present invention also pertain to the method as described above (Method D), wherein after the step of producing, plant material comprising the sialylated protein of interest is orally administered to a subject. For example, after the step of producing, the plant or portion of the plant may be minimally processed to produce minimally processed plant material, and the minimally processed plant material comprising the sialylated protein of interest orally administered to a subject.

As described herein, the expression in plants of Neu5Ac-synthesising enzymes, Neu5Ac lyase and NeuB2, results in the accumulation of functional enzymes within plant tissues, Neu5Ac-synthesising enzymes may be expressed in any plant, for example but not limited to tobacco and *Medicago*

*sativa* (alfalfa), the perennial legume crop that benefits from several agronomic advantages for molecular farming applications (Busse et al., 2001).

This summary of the invention does not necessarily describe all features of the invention.

BRIEF DESCRIPTION OF THE DRAWINGS

These and other features of the invention will become more apparent from the following description in which reference is made to the appended drawings wherein.

DETAILED DESCRIPTION

Figure 1:
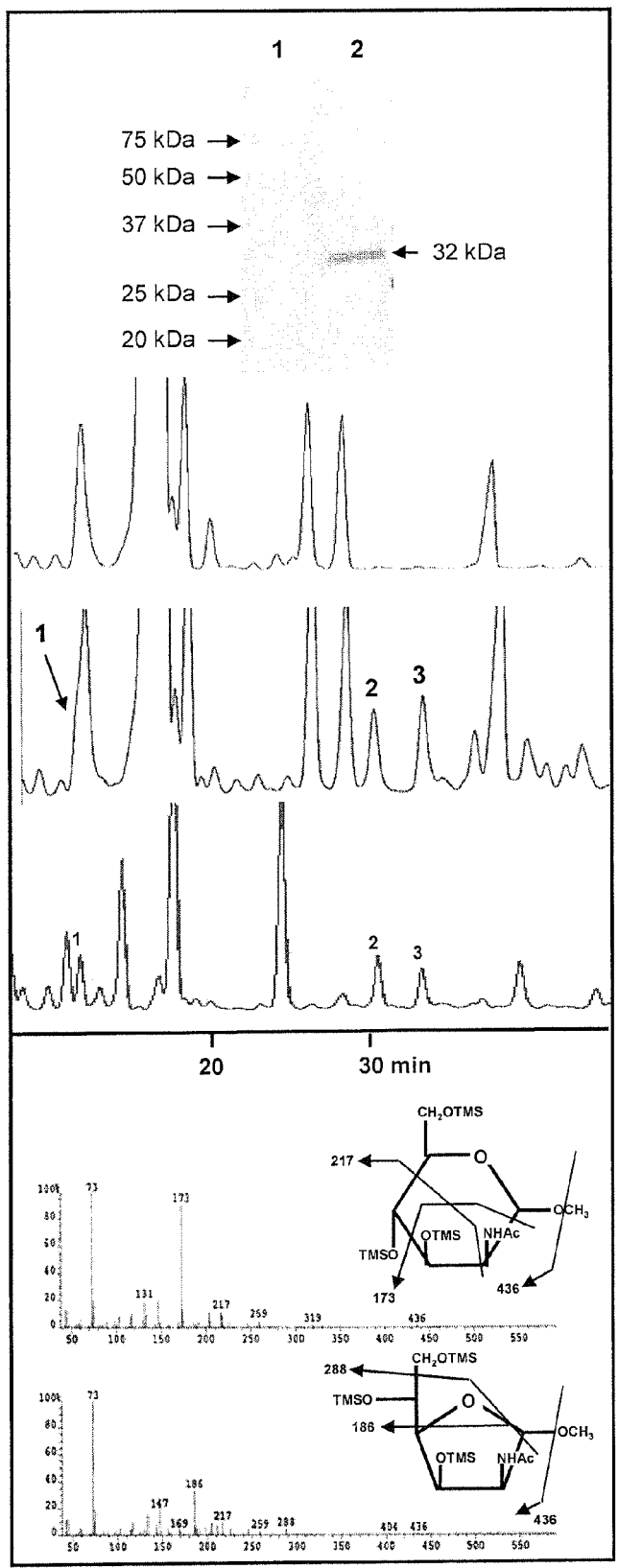
FIG. 1a shows a Western-blot analysis of soluble proteins extracted from wild-type (line 1) or transgenic tobacco BY2 cells expressing the Neu5Ac lyase-FLAG (line 2) using anti-FLAG antibodies.
FIG. 1b and FIG. 1c show a Gas chromatography profiles of the end-products obtained after incubation at pH 7 and 37° C. of cytosolic proteins, isolated from tobacco BY2 cells expressing the Neu5Ac lyase, without (FIG. 1b) or with (FIG. 1c) Neu5Ac.
FIG. 1d shows a GC profile of cytosolic monosaccharides of tobacco BY2 cells expressing the Neu5Ac lyase fed during 48 h at 37° C. with exogenous 10 mM Neu5Ac.
FIG. 1e and FIG. 1f show Electron impact mass spectra of the peak 1 (FIG. 1e), and peaks 2 and 3 (FIG. 1f) detected in profile (FIG. 1c). Main fragment ions of 1-O-methyl persilyl derivatives of D-ManNAc are indicated.

The present invention relates to the synthesis of sialic acid in plants. Furthermore the present invention provides methods and plants that express sialic acid, and sialylated proteins produced from these plants.

The following description is of a preferred embodiment.

The present invention provides a method for the synthesis N-acetyl neuraminic acid (Neu5Ac) within plants. Neu5Ac lyase catabolize sialic acids in bacteria by catalysing the cleavage of Neu5Ac into ManNAc and pyruvate in a reversible reaction. As this reaction is reversible, Neu5Ac lyase may be used to synthesis of Neu5Ac in the presence of the appropriate precursors. An alternate method for the production of Neu5Ac involves the use of Neu5Ac synthase. Neu5Ac synthase catalyzes the formation of Neu5Ac by condensation of D-ManNAc and PEP.

Therefore, the present invention provides a method of synthesizing Neu5Ac comprising, providing a plant comprising a nucleotide sequence encoding Neu5Ac synthase or Neu5Ac lyase, the nucleotide sequence operatively linked with a regulatory region that is active in the plant, growing the plant, and expressing the nucleotide sequence to synthesize Neu5Ac. Alternatively, the method may involve transient production of Neu5Ac within a plant, or a portion of the plant.

The Neu5Ac so produced may be recovered from the plant and used for sialylation of proteins in vitro, using processes known within the art. Alternatively, the Neu5Ac may be used as an endogenous substrate for the sialylation of a protein of interest that is co-expressed within the plant.

If desired, the levels of substrate for the synthesis of Neu5Ac within the plant, including but not limited to N-acetylmannosamine (D-ManNAC), may be increased by co-expressing within the plant one or more than one additional nucleotide sequence encoding one or more than one of an epimerase, a CMP-Neu5Ac synthase, and a CMP-Neu5Ac transporter. For example, ManNAc may be synthesized by expressing within a plant, UDP-GlcNAc 2-epimerase, for example a bacterial UDP-GlcNAc 2-epimerase, or an epimerase form other sources, which converts endogenous UDP-GlcNAc into ManNAc. Alternatively, ManNAc-6-phosphate may be produced, followed by hydrolysis with a phosphatase. With this approach GlcNAc-6-phosphate 2-epimerase, for example a bacterial GlcNAc-6-phosphate 2-epimerase, or a mammalian UDP-GlcNAc 2-epimerase/ManNAc kinase is expressed within a plant. By co-expressing this second nucleotide sequence along with the expression of the nucleotide sequence encoding Neu5Ac synthase or Neu5Ac lyase, increased levels of Neu5Ac may be produced. However, the need for co-expressing one or more of the above nucleotide sequences may depend upon the host plant selected, as endogenous activities of one or more of these enzymes may be present within the plant.

To ensure sialylation of N-glycans from cytosolic sialic acid, bacterial or mammalian CMP-Neu5Ac synthase, mammalian CMP-Neu5Ac transporter, mammalian galactosyltransferase, (for the addition of galactose, before sialic acid can be transferred to N-glycans). and mammalian sialyltransferase may be co-expressed within a plant. Neu5Ac produced within the plant according to the present invention may be used as a substrate for the synthesis of CMP-N-acetylneuraminic acid (CMP-Neu5Ac) via CMP-Neu5Ac synthase, the CMP-Neu5Ac is then used as a substrate for the sialylation of a protein of interest that is also co-expressed within the plant. In this case the plant may also comprise a nucleotide sequence encoding a sialyltransferase. Expression of a mammalian sialyltransferase, and mammalian CMP-Neu5Ac synthase in plants has been demonstrated (Wee et al., 1998, Misaki, R., et al., 2006, which are incorporated herein by reference). However, the need for co-expressing one or more of the above nucleotide sequences may depend upon the host plant selected, as endogenous activities of one or more of these enzymes may be present within the plant.

In the cases where nucleotide sequences are co-expressed within the plant, each of the desired nucleotide sequences may be introduced into the plant using standard transformation techniques, transient transformation techniques, or two plants, each expressing one or more of the desired nucleotide sequences may be crossed to obtain a plant that co-expresses the required combination of nucleotide sequences.

Therefore, the present invention also provides a method for producing a plant that may be used as a platform for the production of a sialylated protein of interest. This method comprises, providing a plant that expresses one or more than one first nucleotide sequence encoding Neu5Ac synthase, Neu5Ac lyase, an epimerase, a CMP-Neu5Ac synthase, a CMP-Neu5Ac transporter, a galactosyltransferase, and a sialyltransferase, and expressing the one or more nucleotide sequence. In order to produce the protein of interest, either a second nucleotide sequence encoding the protein of interest is introduced into the platform plant using standard techniques, for example transformation, and the second nucleotide sequence is expressed, or the platform plant is crossed with a plant expressing the protein of interest so that the protein of interest produced within the progeny of the crossed plants is sialylated.

The present invention also provides a method for producing a protein of interest comprising, providing a plant that expresses one or more than one first nucleotide sequence encoding Neu5Ac synthase, Neu5Ac lyase, an epimerase, a CMP-Neu5Ac synthase, a CMP-Neu5Ac transporter, a galactosyltransferase, and a sialyltransferase, and a second nucleotide sequence encoding the protein of interest, growing the plant, and expressing the first and second nucleotide sequences thereby producing the protein of interest, wherein the protein of interest is sialylated. Preferably, the protein of interest that is sialylated comprises di, tri or tetra antennary N-glycans. The sialylated protein may be extracted from the plant, and if desired, the sialylated protein may be isolated and purified using standard methods. Again, the plants may be either stably transformed with the desired constructs, or the plant or portion of the plant may be transiently transformed with the desired constructs.

The nucleotide sequences encoding Neu5Ac synthase, Neu5Ac lyase, epimerase, CMP-Neu5Ac synthase, a CMP-Neu5Ac transporter, a galactosyltransferase, and sialyltransferase may be codon optimized to increase the level of expression within the plant. By codon optimization it is meant the selection of appropriate DNA nucleotides for the synthesis of oligonucleotide building blocks, and their subsequent enzymatic assembly, of a structural gene or fragment thereof in order to approach codon usage within plants.

In order to optimize the expression of the foreign sequence within a plant, the nucleotide sequence, which may be a wild type or synthetic sequence may be used or altered as required so that the corresponding protein, for example Neu5Ac synthase, Neu5Ac lyase, epimerase, CMP-Neu5Ac synthase, CMP-Neu5Ac transporter, galactosyltransferase, sialyltransferase, the protein of interest, or a combination thereof, is produced at a level higher than would be produced when encoded by the un-modified nucleotide sequence. For example, which is not to be considered limiting, the sequence may be a synthetic sequence, optimized for codon usage within a plant, comprising at least about 80% homology with the wild type sequence, as determined using sequence comparison techniques for example but not limited to BLAST (available through GenBank; using default parameters). It is also contemplated that fragments or portions of the sequence encoding the protein of interest, or derivatives thereof, that exhibit useful biological properties, for example but not limited to antigenic properties, may be expressed within plant tissues.

In order to maximize expression levels and transgene protein production of Neu5Ac synthase, Neu5Ac lyase, epimerase, CMP-Neu5Ac synthase, CMP-Neu5Ac transporter, galactosyltransferase, sialyltransferase, and a protein of interest, the nucleic acid sequence may be examined and the coding region modified to optimize for expression of the gene in plants, using a procedure similar to that outlined by Sardana et al. (Plant Cell Reports 15:677-681; 1996). A table of codon usage from highly expressed genes of dicotyledonous plants is available from several sources including Murray et al. (Nuc Acids Res. 17:477-498; 1989).

Therefore, the present invention provides a method of synthesizing sialic acid comprising, providing a plant comprising a nucleotide sequence encoding N-acetyl neuraminic acid (Neu5Ac) synthase or Neu5Ac lyase, the nucleotide sequence operatively linked with a regulatory region that is active in the plant, growing the plant, and expressing the nucleotide sequence thereby synthesizing sialic acid. The nucleotide sequence encoding Neu5Ac synthase or Neu5Ac lyase may be codon optimized for expression within the plant. Furthermore, in the step of providing, the plant may further comprise a second nucleotide sequence encoding one or more than one of an epimerase, a CMP-Neu5Ac synthase, or a CMP-Neu5Ac transporter, operatively linked to one or more than one second regulatory region active within the plant, and the second nucleotide sequence is co-expressed along with the expression of the nucleotide sequence. The second nucleotide sequence encoding one or more than one of the epimerase, CMP-Neu5Ac synthase, or CMP-Neu5Ac transporter, may be codon optimized for expression within the plant.

Additionally, the present invention provides a method of producing a protein of interest comprising providing a plant that expresses one or more than one first nucleotide sequence encoding Neu5Ac synthase, Neu5Ac lyase, an epimerase, a CMP-Neu5Ac synthase, a CMP-Neu5Ac transporter, a galactosyltransferase, a sialyltransferase, and a second nucleotide sequence encoding the protein of interest, growing the plant, and expressing the first and second nucleotide sequences thereby producing the protein of interest. The one or more than one first nucleotide sequence encoding Neu5Ac synthase, Neu5Ac lyase, an epimerase, a CMP-Neu5Ac synthase, a CMP-Neu5Ac transporter, a galactosyltransferase, a sialyltransferase, a second nucleotide sequence encoding the protein of interest, or both the first nucleotide sequence, and the second nucleotide sequence may be codon optimized for expression within the plant.

Furthermore, the present invention pertains to a plant, a plant cell, or a seed, comprising a nucleotide sequence encoding Neu5Ac synthase or Neu5Ac lyase operatively linked with a regulatory region that is active in the plant. The plant, plant cell, or seed may further comprise a second nucleotide sequence encoding one or more than one of an epimerase, a CMP-Neu5Ac synthase, a CMP-Neu5Ac transporter, a galactosyltransferase, and a sialyltransferase, operatively linked to one or more than one second regulatory region active within the plant. The nucleotide sequence encoding Neu5Ac synthase or Neu5Ac lyase, the second nucleotide sequence encoding one or more than one of the epimerase, CMP-Neu5Ac synthase, or CMP-Neu5Ac transporter, or both the nucleotide sequence and the second nucleotide sequence, may be codon optimized for expression within the plant, plant cell or plant seed.

The present invention also includes a plant, a plant cell, or a seed, comprising one or more than one first nucleotide sequence encoding Neu5Ac synthase, Neu5Ac lyase, an epimerase, a CMP-Neu5Ac synthase, a CMP-Neu5Ac transporter, a galactosyltransferase, and a sialyltransferase, and a second nucleotide sequence encoding a protein of interest, the first and second nucleotide sequence operatively linked with one or more than one regulatory region that is active in the plant. The one or more than one first nucleotide sequence encoding Neu5Ac synthase, Neu5Ac lyase, an epimerase, a CMP-Neu5Ac synthase, a CMP-Neu5Ac transporter, a galactosyltransferase, a sialyltransferase, a second nucleotide sequence encoding the protein of interest, or both the first nucleotide sequence, and the second nucleotide sequence may be codon optimized for expression within the plant.

By "operatively linked" it is meant that the particular sequences interact either directly or indirectly to carry out an intended function, such as mediation or modulation of gene expression. The interaction of operatively linked sequences may, for example, be mediated by proteins that interact with the operatively linked sequences. A transcriptional regulatory region and a sequence of interest are operably linked when the sequences are functionally connected so as to permit transcription of the sequence of interest to be mediated or modulated by the transcriptional regulatory region.

By the term "plant matter", it is meant any material derived from a plant. Plant matter may comprise an entire plant, tissue, cells, or any fraction thereof. Further, plant matter may comprise intracellular plant components, extracellular plant components, liquid or solid extracts of plants, or a combination thereof. Further, plant matter may comprise plants, plant cells, tissue, a liquid extract, or a combination thereof, from plant leaves, stems, fruit, roots or a combination thereof. Plant matter may comprise a plant or portion thereof which has not be subjected to any processing steps. However, it is also contemplated that the plant material may be subjected to minimal processing steps as defined below, or more rigorous processing, including partial or substantial protein purification using techniques commonly known within the art including, but not limited to chromatography, electrophoresis and the like.

By the term "minimal processing" it is meant plant matter, for example, a plant or portion thereof comprising a protein of interest which is partially purified to yield a plant extract, homogenate, fraction of plant homogenate or the like. Partial purification may comprise, but is not limited to disrupting plant cellular structures thereby creating a composition comprising soluble plant components, and insoluble plant components which may be separated for example, but not limited to, by centrifugation, filtration or a combination thereof. In this regard, proteins secreted within the extracellular space of leaf or other tissues could be readily obtained using vacuum or centrifugal extraction, or tissues could be extracted under pressure by passage through rollers or grinding or the like to squeeze or liberate the protein free from within the extracellular space. Minimal processing could also involve preparation of crude extracts of soluble proteins, since these preparations would have negligible contamination from secondary plant products. Further, minimal processing may involve aqueous extraction of soluble protein from leaves, followed by precipitation with any suitable salt. Other methods may include large scale maceration and juice extraction in order to permit the direct use of the extract.

The plant matter, in the form of plant material or tissue may be orally delivered to a subject. The plant matter may be administered as part of a dietary supplement, along with other foods, or encapsulated. The plant matter or tissue may also be concentrated to improve or increase palatability, or provided along with other materials, ingredients, or pharmaceutical excipients, as required.

It is contemplated that a plant comprising the heterologous protein of interest may be administered to a subject, for example an animal or human, in a variety of ways depending upon the need and the situation. For example, if the protein is orally administered, the plant tissue may be harvested and directly feed to the subject, or the harvested tissue may be dried prior to feeding, or an animal may be permitted to graze on the plant with no prior harvest taking place. It is also considered within the scope of this invention for the harvested plant tissues to be provided as a food supplement within animal feed. If the plant tissue is being feed to an animal with little or not further processing it is preferred that the plant tissue being administered is edible. Furthermore, the protein of interest obtained from the plant may be extracted prior to its use as a food supplement, in either a crude, partially purified, or purified form. In this latter case, the protein may be produced in either edible or non-edible plants.

As described in more detail in the Examples, Neu5Ac lyase, and Neu5Ac lyase-FLAG (Neu5Ac lyase tagged at its C-terminus with a FLAG epitope to allow immunodetection of the recombinant protein in transformants) were introduced into plants. Western-blot analysis, using anti-FLAG antibodies, demonstrated that a protein of $MW_r$ 32 kDa was present in the transformed cells (FIG. 1a). Furthermore both in vitro and in vivo lyase activity was detectable in extracts obtained from, or plants expressing either Neu5Ac lyase or Neu5Ac lyase-FLAG. No endogenous lyase activity was detected in non-transformed plants. However, the synthesis of Neu5Ac using recombinantly produced Neu5Ac lyase, in the presence of D-ManNAc and pyruvate was observed (see FIG. 2b). Therefore, recombinantly expressed Neu5Ac lyase is biologically active in planta.

Neu5Ac synthase (for example, but not limited to NeuB2) and Neu5Ac synthase-FLAG (Neu5Ac synthase tagged at its C-terminus with a FLAG epitope to allow immunodetection of the recombinant protein in transformants) were introduced into plants. Western-blot analysis, using anti-FLAG antibodies, demonstrated that a protein of $MW_r$ 37 kDa was present in the transformed cells. Both in vitro and in vivo synthase activity was detectable in extracts obtained from, or plants expressing either Neu5Ac synthase or Neu5Ac synthase-FLAG. No endogenous synthase activity was detected in non-transformed plants. However, the synthesis of Neu5Ac using recombinantly produced Neu5Ac synthase in the presence of D-ManNAc and PEP was observed (see FIGS. 3b, 3c). Therefore, recombinantly expressed Neu5Ac synthase is biologically active in planta.

An "analogue" or "derivative" includes any substitution, deletion, or addition to the silencing nucleotide sequence, provided that the nucleotide sequence retains the property of silencing expression of a target gene or sequence, reducing expression of a target sequence, or reducing synthesis or activity of a protein encoded by the target sequence. For example, derivatives, and analogues of nucleic acid sequences typically exhibit greater than 80% similarity with, a silencing nucleic acid sequence. Sequence similarity, may be determined by use of the BLAST algorithm (GenBank: ncbi.nlm.nih.gov/cgi-bin/BLAST/), using default parameters (Program: blastn; Database: nr; Expect 10; filter: low complexity; Alignment: pairwise; Word size: 11). Analogs, or derivatives thereof, also include those nucleotide sequences that hybridize under stringent hybridization conditions (see Maniatis et al., in Molecular Cloning (A Laboratory Manual), Cold Spring Harbor Laboratory, 1982, p. 387-389, or Ausubel, et al. (eds), 1989, *Current Protocols in Molecular Biology*, Vol. 1, Green Publishing Associates, Inc., and John Wiley & Sons, Inc., New York, at p. 2.10.3) to any one of the sequences described herein, provided that the sequences exhibit the property of silencing expression of a target gene. An example of one such stringent hybridization conditions may be hybridization with a suitable probe, for example but not limited to, a [gama-$^{32}$P]dATP labelled probe for 16-20 hrs at 65EC in 7% SDS, 1 mM EDTA, 0.5M Na₂HPO₄, pH 7.2. Followed by washing in 5% SDS, 1 mM EDTA 40 mM Na₂HPO₄, pH 7.2 for 30 min followed by washing in 1% SDS, 1 mM EDTA 40 mM Na₂HPO₄, pH 7.2 for 30 min. Washing in this buffer may be repeated to reduce background.

By "regulatory region" "regulatory element" or "promoter" it is meant a portion of nucleic acid typically, but not always, upstream of the protein coding region of a gene, which may be comprised of either DNA or RNA, or both DNA and RNA. When a regulatory region is active, and in operative association, or operatively linked, with a gene of interest, this may result in expression of the gene of interest. A regulatory element may be capable of mediating organ specificity, or controlling developmental or temporal gene activation. A "regulatory region" includes promoter elements, core promoter elements exhibiting a basal promoter activity, elements that are inducible in response to an external stimulus, elements that mediate promoter activity such as negative regulatory elements or transcriptional enhancers. "Regulatory region", as used herein, also includes elements that are active following transcription, for example, regulatory elements that modulate gene expression such as translational and transcriptional enhancers, translational and transcriptional repressors, upstream activating sequences, and mRNA instability determinants. Several of these latter elements may be located proximal to the coding region.

In the context of this disclosure, the term "regulatory element" or "regulatory region" typically refers to a sequence of DNA, usually, but not always, upstream (5') to the coding sequence of a structural gene, which controls the expression of the coding region by providing the recognition for RNA polymerase and/or other factors required for transcription to start at a particular site. However, it is to be understood that other nucleotide sequences, located within introns, or 3' of the sequence may also contribute to the regulation of expression of a coding region of interest. An example of a regulatory element that provides for the recognition for RNA polymerase or other transcriptional factors to ensure initiation at a particular site is a promoter element. Most, but not all, eukaryotic promoter elements contain a TATA box, a conserved nucleic acid sequence comprised of adenosine and thymidine nucleotide base pairs usually situated approximately 25 base pairs upstream of a transcriptional start site. A promoter element comprises a basal promoter element, responsible for the initiation of transcription, as well as other regulatory elements (as listed above) that modify gene expression.

There are several types of regulatory regions, including those that are developmentally regulated, inducible or constitutive. A regulatory region that is developmentally regulated, or controls the differential expression of a gene under its control, is activated within certain organs or tissues of an organ at specific times during the development of that organ or tissue. However, some regulatory regions that are developmentally regulated may preferentially be active within certain organs or tissues at specific developmental stages, they may also be active in a developmentally regulated manner, or at a basal level in other organs or tissues within the plant as well. Examples of tissue-specific regulatory regions, for example see-specific a regulatory region, include the napin promoter, and the cruciferin promoter (Rask et al., 1998, J. Plant Physiol. 152: 595-599; Bilodeau et al., 1994, Plant Cell 14: 125-130).

An inducible regulatory region is one that is capable of directly or indirectly activating transcription of one or more DNA sequences or genes in response to an inducer. In the absence of an inducer the DNA sequences or genes will not be transcribed. Typically the protein factor that binds specifically to an inducible regulatory region to activate transcription may be present in an inactive form, which is then directly or indirectly converted to the active form by the inducer. However, the protein factor may also be absent. The inducer can be a chemical agent such as a protein, metabolite, growth regulator, herbicide or phenolic compound or a physiological stress imposed directly by heat, cold, salt, or toxic elements or indirectly through the action of a pathogen or disease agent such as a virus. A plant cell containing an inducible regulatory region may be exposed to an inducer by externally applying the inducer to the cell or plant such as by spraying, watering, heating or similar methods. Inducible regulatory elements may be derived from either plant or non-plant genes (e.g. Gatz, C. and Lenk, I. R. P., 1998, Trends Plant Sci. 3, 352-358; which is incorporated by reference). Examples, of potential inducible promoters include, but not limited to, tetracycline-inducible promoter (Gatz, C., 1997, Ann. Rev. Plant Physiol. Plant Mol. Biol. 48, 89-108; which is incorporated by reference), steroid inducible promoter (Aoyama, T. and Chua, N. H., 1997, Plant J. 2, 397-404; which is incorporated by reference) and ethanol-inducible promoter (Salter, M. G., et al, 1998, Plant Journal 16, 127-132; Caddick, M. X., et al, 1998, Nature Biotech. 16, 177-180, which are incorporated by reference) cytokinin inducible IB6 and CKI1 genes (Brandstatter, I. and Kieber, J. J., 1998, Plant Cell 10, 1009-1019; Kakimoto, T., 1996, Science 274, 982-985; which are incorporated by reference) and the auxin inducible element, DR5 (Ulmasov, T., et al., 1997, Plant Cell 9, 1963-1971; which is incorporated by reference).

A constitutive regulatory region directs the expression of a gene throughout the various parts of a plant and continuously throughout plant development. Examples of known constitutive regulatory elements include promoters associated with the CaMV 35S transcript. (Odell et al., 1985, Nature, 313: 810-812), the rice actin 1 (Zhang et al, 1991, Plant Cell, 3: 1155-1165), actin 2 (An et al., 1996, *Plant J.,* 10: 107-121), or tms 2 (U.S. Pat. No. 5,428,147, which is incorporated herein by reference), and triosephosphate isomerase 1 (Xu et. al., 1994, Plant Physiol. 106: 459-467) genes, the maize ubiquitin 1 gene (Cornejo et al, 1993, Plant Mol. Biol. 29: 637-646), the *Arabidopsis* ubiquitin 1 and 6 genes (Holtorf et al, 1995, Plant Mol. Biol. 29: 637-646), and the tobacco translational initiation factor 4A gene (Mandel et al, 1995 Plant Mol. Biol. 29: 995-1004). The term "constitutive" as used herein does not necessarily indicate that a gene under control of the constitutive regulatory region is expressed at the same level in all cell types, but that the gene is expressed in a wide range of cell types even though variation in abundance is often observed.

The one or more than one nucleotide sequence of the present invention may be expressed in any suitable plant host that is transformed by the nucleotide sequence, or constructs, or vectors of the present invention. Examples of suitable hosts include, but are not limited to, agricultural crops including alfalfa, canola, *Brassica* spp., maize, tobacco, alfalfa, potato, *ginseng*, pea, oat, rice, soybean, wheat, barley, sunflower, and cotton.

Therefore, the present invention also provides for a plant, a plant cell, or a seed comprising a nucleotide sequence encoding Neu5Ac synthase or Neu5Ac lyase operatively linked with a regulatory region that is active in the plant. Furthermore, the plant, the plant cell or the seed may comprising a second nucleotide sequence encoding one or more than one of an epimerase, a CMP-Neu5Ac synthase, a CMP-Neu5Ac transporter, a galactosyltransferase, and a sialyltransferase, operatively linked to one or more than one second regulatory region active within the plant.

The present invention also provides a plant, a plant cell, or a seed, comprising one or more than one first nucleotide sequence encoding Neu5Ac synthase, Neu5Ac lyase, an epimerase, a CMP-Neu5Ac synthase, a CMP-Neu5Ac transporter, a galactosyltransferase, and a sialyltransferase, and a second nucleotide sequence encoding a protein of interest, the first and second nucleotide sequence operatively linked with one or more than one regulatory region that is active in the plant.

The one or more chimeric genetic constructs of the present invention can further comprise a 3' untranslated region. A 3' untranslated region refers to that portion of a gene comprising a DNA segment that contains a polyadenylation signal and any other regulatory signals capable of effecting mRNA processing or gene expression. The polyadenylation signal is usually characterized by effecting the addition of polyadenylic acid tracks to the 3' end of the mRNA precursor. Polyadenylation signals are commonly recognized by the presence of homology to the canonical form 5' AATAAA-3' although variations are not uncommon. One or more of the chimeric genetic constructs of the present invention can also include further enhancers, either translation or transcription enhancers, as may be required. These enhancer regions are well known to persons skilled in the art, and can include the ATG initiation codon and adjacent sequences. The initiation codon must be in phase with the reading frame of the coding sequence to ensure translation of the entire sequence.

Non-limiting examples of suitable 3' regions are the 3' transcribed non-translated regions containing a polyadenylation signal of *Agrobacterium* tumor inducing (Ti) plasmid genes, such as the nopaline synthase (Nos gene) and plant genes such as the soybean storage protein genes and the small subunit of the ribulose-1,5-bisphosphate carboxylase (ssRUBISCO) gene.

To aid in identification of transformed plant cells, the constructs of this invention may be further manipulated to include plant selectable markers. Useful selectable markers include enzymes that provide for resistance to chemicals such as an antibiotic for example, gentamycin, hygromycin, kanamycin, or herbicides such as phosphinothrycin, glyphosate, chlorosulfuron, and the like. Similarly, enzymes providing for production of a compound identifiable by colour change such as GUS (beta-glucuronidase), or luminescence, such as luciferase or GFP, may be used.

Also considered part of this invention are transgenic plants, plant cells or seeds containing the chimeric gene construct of the present invention. Methods of regenerating whole plants from plant cells are also known in the art. In general, transformed plant cells are cultured in an appropriate medium, which may contain selective agents such as antibiotics, where selectable markers are used to facilitate identification of transformed plant cells. Once callus forms, shoot formation can be encouraged by employing the appropriate plant hormones in accordance with known methods and the shoots transferred to rooting medium for regeneration of plants. The plants may then be used to establish repetitive generations, either from seeds or using vegetative propagation techniques. Transgenic plants can also be generated without using tissue cultures.

The regulatory elements of the present invention may also be combined with coding region of interest for expression within a range of host organisms that are amenable to transformation, or transient expression. Such organisms include, but are not limited to plants, both monocots and dicots, for example but not limited to corn, cereal plants, wheat, barley, oat, tobacco, *Brassica*, soybean, bean, pea, alfalfa, potato, tomato, *ginseng*, and *Arabidopsis*.

Methods for transient expression, transformation, and regeneration of these organisms are established in the art and known to one of skill in the art. The method of obtaining transformed and regenerated plants is not critical to the present invention.

By "transformation" it is meant the interspecific transfer of genetic information that is manifested genotypically, phenotypically, or both. The interspecific transfer of genetic information from a chimeric construct to a host may be heritable and the transfer of genetic information considered stable, or the transfer may be transient and the transfer of genetic information is not inheritable. The present invention further includes a suitable vector comprising the chimeric gene construct suitable for use with either stable or transient expression systems.

The constructs of the present invention can be introduced into plant cells using Ti plasmids, Ri plasmids, plant virus vectors, direct DNA transformation, micro-injection, electroporation, etc. For reviews of such techniques see for example Weissbach and Weissbach, *Methods for Plant Molecular Biology*, Academy Press, New York VIII, pp. 421-463 (1988); Geierson and Corey, *Plant Molecular Biology*, 2d Ed. (1988); and Miki and Iyer, *Fundamentals of Gene Transfer in Plants*. In *Plant Metabolism,* 2d Ed. D T. Dennis, D H Turpin, D D Lefebrve, D B Layzell (eds), Addison Wesly, Langmans Ltd. London, pp. 561-579 (1997). Other methods include direct DNA uptake, the use of liposomes, electroporation, for example using protoplasts, micro-injection, microprojectiles or whiskers, and vacuum infiltration. See, for example, Bilang, et al. (Gene 100: 247-250 (1991), Scheid et al. (Mol. Gen. Genet. 228: 104-112, 1991), Guerche et al. (Plant Science 52: 111-116, 1987), Neuhause et al. (Theor. Appl Genet. 75: 30-36, 1987), Klein et al., Nature 327: 70-73 (1987); Howell et al. (Science 208: 1265, 1980), Horsch et al. (Science 227: 1229-1231, 1985), DeBlock et al., Plant Physiology 91: 694-701, 1989), Methods for Plant Molecular Biology (Weissbach and Weissbach, eds., Academic Press Inc., 1988), Methods in Plant Molecular Biology (Schuler and Zielinski, eds., Academic Press Inc., 1989), Liu and Lomonossoff (J Virol Meth, 105:343-348, 2002), U.S. Pat. Nos. 4,945,050; 5,036, 006; and 5,100,792, U.S. patent application Ser. No. 08/438, 666, filed May 10, 1995, and Ser. No. 07/951,715, filed Sep. 25, 1992, (all of which are hereby incorporated by reference).

As described below, transient expression methods may be used to express the constructs of the present invention (see Liu and Lomonossoff, 2002, Journal of Virological Methods, 105:343-348; which is incorporated herein by reference). These methods may include, for example, but are not limited to, a method of Agro-inoculation or Agro-infiltration, however, other transient methods may also be used as noted above. With either Agro-inoculation or Agro-infiltration, a mixture of Agrobacteria comprising the desired nucleic acid enter the intercellular spaces of the a tissue, for example the leaves, aerial portion of the plant (including stem, leaves and flower), other portion of the plant (stem, root, flower), or the whole plant. After crossing the epidermis the Agrobacteria infect and transfer t-DNA copies into the cells. The t-DNA is episomally transcribed and the mRNA translated, leading to the production of the protein of interest in infected cells, however, the passage oft-DNA inside the nucleus is transient.

By "gene of interest", "nucleotide sequence of interest", or "coding region of interest", it is meant any gene, nucleotide sequence, or coding region that is to be expressed within a host organism, for example a plant. These terms are used interchangeably. Such a nucleotide sequence of interest may include, but is not limited to, a gene or coding region whose product is an industrial enzyme, a protein supplement, a nutraceutical, a value-added product, or a fragment thereof for feed, food, or both feed and food use. A nucleotide sequence, or coding region of interest may also include a gene that encodes a pharmaceutically active protein, for example growth factors, growth regulators, antibodies, antigens, and fragments thereof, or their derivatives useful for immunization or vaccination and the like. Such proteins include, but are not limited to, interleukins, for example one or more than one of IL-1 to IL-24, IL-26 and IL-27, cytokines, Erythropoietin (EPO), insulin, G-CSF, GM-CSF, hPG-CSF, M-CSF or combinations thereof, interferons, for example, interferon-alpha, interferon-beta, interferon-gama, blood clotting factors, for example, Factor VIII, Factor IX, or tPA hGH, receptors, receptor agonists, antibodies, neuropolypeptides, insulin, vaccines, growth factors for example but not limited to epidermal growth factor, keratinocyte growth factor, transformation growth factor, growth regulators, antigens, autoantigens, fragments thereof, or combinations thereof.

If the gene of interest encodes a product that is directly or indirectly toxic to the plant, then by using the method of the present invention, such toxicity may be reduced throughout the plant by selectively expressing the gene of interest within a desired tissue or at a desired stage of plant development.

The coding region of interest or the nucleotide sequence of interest may be expressed in any suitable plant host which is either transformed or comprises the nucleotide sequences, or nucleic acid molecules, or genetic constructs, or vectors of the present invention. Examples of suitable hosts include, but are not limited to, *Arabidopsis*, agricultural crops including for example canola, *Brassica* spp., maize, tobacco, alfalfa, potato, ginseng, pea, oat, rice, soybean, wheat, barley, sunflower, and cotton.

Sialic acid synthesis, for example, Neu5Ac synthesis, in plants was demonstrated by expressing recombinant Neu5Ac lyase or Neu5Ac synthase. Neu5Ac lyase from *E. coli* and NeuB2 from *C. jejuni* were each expressed in the cytosol of tobacco BY2 cells, alfalfa plants by *Agrobacterium*-mediated transformation, or when transiently expressed in plant cells. No degradation of the recombinant proteins was observed indicating that these enzymes are stable in this compartment. The Neu5Ac lyase expressed in BY2 cells was able to catalyse the cleavage of Neu5Ac into D-ManNAc and pyruvate in a reversible reaction. The synthesis of Neu5Ac in presence of pyruvate and ManNAc was also observed. Neu5Ac lyase was biologically active at pH 7 and over a 25-37° C. range which is consistent with both pH of the plant cytosol and temperature of most important crops. Furthermore, feeding experiments carried out in presence of exogenous Neu5Ac demonstrated that the enzyme was functional in planta.

The Neu5Ac synthase, NeuB2 from *C. jejuni*, when expressed in tobacco BY2 cells was observed to synthesize Neu5Ac in presence of D-ManNAc and PEP. Expression of NeuB2 in alfalfa plants also resulted in an accumulation of a functional enzyme. Therefore, expression of a microbial Neu5Ac lyase or Neu5Ac synthase in plants results in the production in the cytosol of enzymes able to synthesise Neu5Ac.

An epimerase able to convert the endogenous GlcNAc into ManNAc, may be co-expressed in plants in order to supply Neu5Ac lyase or Neu5Ac synthase with the appropriate aminosugar substrate. In this regard, the expression of a functional CMP-Neu5Ac synthase and CMP-Neu5Ac transporter in tobacco BY2 cells has been reported (Misaki et al., 2006). By co-expressing CMP-Neu5Ac synthase, CMP-Neu5Ac transporter, or both CMP-Neu5Ac synthase and CMP-Neu5Ac transporter, along with NeuB2, production of Neu5Ac may be enhanced. N-acetylmannosamine (ManNAc) synthesis within a plant may be achieved via several methods. For example, ManNAc may be synthesized by expressing within a plant, UDP-GlcNAc 2-epimerase, for example a bacterial UDP-GlcNAc 2-epimerase, which converts UDP-GlcNAc into ManNAc in an irreversible reaction. UDP-GlcNAc is present in the cytosol since it feeds the N-glycans synthesis pathway. ManNAc synthesis may also be achieved by expressing a GlcNAc-2 epimerase from other sources. Alternatively, ManNAc-6-phosphate may be formed, followed by hydrolysis with a phosphatase (in transgenic plants). With this approach GlcNAc-6-phosphate 2-epimerase, for example a bacterial GlcNAc-6-phosphate 2-epimerase, or a mammalian UDP-GlcNAc 2-epimerase/ManNAc kinase is expressed within a plant.

To ensure sialylation of N-glycans from cytosolic sialic acid, bacterial or mammalian CMP-Neu5Ac synthase, mammalian CMP-Neu5Ac transporter, a mammalian galactosyltransferase, and mammalian sialyltransferase may be co-expressed within a plant (Misaki, R., et. Al. 2006).

The present invention will be further illustrated in the following examples.

EXAMPLES

Methods

Polyclonal antibodies directed against the synthetic FLAG sequence polypeptide (Asp-Tyr-Lys-Asp-Asp-Asp-Asp-Lys; SEQ ID NO:1) were prepared in rabbits at Eurogentec (Seraing, Belgium). $C_{18}$ Bond-Elut cartridges were from Varian (Sugarland, Tex.). *Escherichia coli* DH5-alpha and *Agrobacterium tumefaciens* LBA4404 were used for cloning experiments and transformation of tobacco cells or *M. sativa*, respectively. *Nicotiana tabacum* cv Bright Yellow 2 (BY-2) cells were grown as described in Gomord et al. (1998).

Cloning of Neu5Ac Lyase and neuB2 Genes and Construction of the Plant Expression Vector Neu5Ac lyase and neuB2 genes were amplified by PCR. The gene for Neu5Ac lyase was amplified from *E. coli* K1 genomic DNA by PCR using primers:

```
Lyase-P1:
                                        (SEQ ID NO: 6)
5'-AATAGGCCATTACGGCCATGGCAACGAATTTACGTGG-3'
and Lyase-P2:
                                        (SEQ ID NO: 7)
5'-AATAGGCCGAGGCGGCCTCACCCGCGCTCTTGCAT-3'.
```

For neuB2 gene, the following primers were used to obtain the DNA fragment:

```
neuB2-P1:
                                         (SEQ ID NO: 8)
5'-AATAGGCCATTACGGCCATGAAAAAAACTTTAATC-3'
and neuB2-P2:
                                         (SEQ ID NO: 9)
5'-AATAGGCCGAGGCGGCCTTACTCACGGATAAGCTC-3'.
```

These amplified DNAs were placed under the cauliflower mosaic virus (CaMV) 35S promoter of plasmid vector pDNR-LIB for the Neu5Ac lyase gene and binary plasmid vector pCAMBIA 2300 for the neuB2 gene, respectively. The expression cassette of CaMV35S promoter, Neu5Ac lyase, and nopaline synthase (Nos) terminator was introduced into plant expression vector pBLTI 121 (Pagny et al., 2000) with kanamycin resistance gene.

To generate the pBLTI Neu5Ac lyase-FLAG and pBLTI neuB2-FLAG plasmids, the following four primers, designed to amplify the genes with the FLAG peptide encoded at the C-terminal end of the proteins were used:

```
Lyase-FLAG-P1:
                                         (SEQ ID NO: 2)
5'-CGGGGTACCAGAGAGATGGCAACGAATTTACGTGGC-3', Lyase-FLAG-P2:
                                         (SEQ ID NO: 3)
5' GCCGAGCTCTCACTTGTCATCGTCATCCTTGTAATCCATCC
CGCGCTCTTGCATCAACTG-3', neuB2-FLAG-P1:
                                         (SEQ ID NO: 4)
5'-CGGGGTACCAGAGAGATGAAAAAAACTTTAATCATCGC-3'
and neuB2-FLAG-P2:
                                         (SEQ ID NO: 5)
5'-GCCGAGCTCTCACTTGTCATCGTCATCCTTGTAATCCATCT
CACGGATAAGCTCATCTTC-3',
```

These amplified sequences were generated by PCR with the following program for 30 cycles: denaturation at 94° C. for 1 min, annealing for 1 min at 58° C., and polymerization at 72° C. for 3 min. PCR products were cloned into pCR®-BLUNT II-TOPO® (Invitrogen). Before expressing the recombinant proteins in plant cells, we confirmed all of the modified cDNA constructs by sequencing. Subsequently, the inserts were digested with KpnI and SacI and then cloned into KpnI-SacI-digested pBLTI 121. Each vector (pBLTI 121 or pCAMBIA 2300) was introduced in *Agrobacterium tumefaciens* strain LBA4404 via heat shock transformation.

Expression in BY2 Cells

Tobacco BY2 cells were maintained in Murashige and Skoog (1962) medium and used for transformation. The pBLTI121-derived constructs were transferred into *Agrobacterium* (LBA4404) (Hofgen and Willmitzer, 1988). Transgenic *Agrobacterium* cells were selected on YEB medium containing 100 µg·mL$^{-1}$ kanamycin and used to transform suspension-cultured cells of tobacco as described in Gomord et al. (1998). Transformants were selected and maintained in MS medium containing antibiotics (kanamycin at 100 µg mL$^{-1}$ and cefotaxime at 250 µg·mL$^{-1}$). Genomic DNA and mRNA were prepared from each transformant, and it was confirmed that objected genes were inserted and expressed in tobacco suspension-cultured cells by PCR and RT-PCR. After immunoscreening, microcalli producing the recombinant proteins were used to initiate suspension cultures of transgenic cells (Gomord et al., 1998).

Expression in Alfalfa Plants

Alfalfa transformation was performed essentially as described in Tian et al., (Tian et al., 2002) with the following modifications. Alfalfa genotype R2336 was transformed using *Agrobacterium tumefaciens* AGL1. The co-culture step was performed with an undiluted culture at 0.8 to 1 OD, and 3% sucrose was used in the Sh2K medium instead of 1.5% sucrose.

Preparation of Cell Extracts for Assay of Neu5Ac Lyase and NeuB2 Activity.

One gram of four day old cultures of BY2 suspension-cultured cells of transformants or 600 mg of fresh leaves of *M. sativa* were harvested and disrupted in Solution A (100 mM HCl buffer (pH=7.4) containing proteinase inhibitors (pepstatine 1 µg·mL$^4$, E64 1 µg·mL$^{-1}$ and PMSF 1 mM, Sigma). Cell extracts were then centrifuged at 10000 g for 10 min at 4° C. and proteins were precipitated with ammonium sulfate (final concentration 80%) and then dialysed against Solution B (100 mM Tris-HCl buffer, pH=7.4 for Neu5Ac lyase assays or pH=8.5 for NeuB2 assays and 10 mM MgCl$_2$) with Spectra/Por® membrane (cut-off 10000 Da). Proteins were then utilised for enzymes assays or immunodetections.

Immunodetection of Neu5Ac Lyase-FLAG and NeuB2-FLAG

The proteins were solubilized in a denaturating buffer (20 mM Tris-HCl pH 6.8, 0.3% β-mercaptoethanol, 5% (v/v) glycerol and 1% (w/v) SDS), boiled for 5 min and separated by SDS-PAGE in 15% polyacrylamide gels. Proteins were then transferred onto a nitrocellulose membrane. For immunodetection, membranes were probed with a rabbit antiserum raised against the FLAG epitope. Proteins were detected by incubation with goat anti-rabbit antibodies conjugated to horseradish peroxidase followed by the revelation using 4-chloronaphtol or by a chemiluminescence reaction.

Neu5Ac Lyase and Synthase Assays

Soluble enzyme activities were assayed by incubating cell extracts with PEP 4 mM, NADH 4 mM, NaHCO$_3$ 20 mM and DTE 10 mM. Oxydation of NADH was measured by a diminution of absorbance at 340 nm after 10 min. Lyase activity of Neu5Ac lyase was assayed by measuring the formation of ManNAc after incubating transformants cells extracts with Neu5Ac. Cells extracts were incubated 2 h at 37° C. in Solution B (100 mM Tris-HCl buffer, pH=7.4 and 10 mM MgCl$_2$) containing proteinase inhibitors (pepstatine 1 µg·mL$^{-1}$, E64 1 µg·mL$^1$ and PMSF 1 mM) and Neu5Ac 40 mM. Synthase activity of Neu5Ac lyase was assayed by measuring the formation of Neu5Ac after incubating transformants cells extracts with ManNAc and pyruvate. Cells extracts were incubated 2 h at 37° C. in Solution B (100 mM HCl buffer, pH=7.4 and 10 mM MgCl$_2$) containing proteinase inhibitors (pepstatine 1 µg·mL$^{-1}$, E64 1 µg·mL$^1$ and PMSF 1 mM) and ManNAc 20 mM and pyruvate 40 mM. Synthase activity of NeuB2 was assayed by measuring the formation of Neu5Ac after incubating transformants cells extracts with ManNAc and PEP. Cells extracts were incubated 2 h at 37° C. in Solution B (100 mM Tris-HCl buffer, pH=7.4 and 10 mM MgCl$_2$) containing proteinase inhibitors (pepstatine 1 µg·mL$^{-1}$, E64 1 µg·mL$^{-1}$ and PMSF 1 mM) and ManNAc 10 mM and PEP 10 mM. The reactions were stopped by heating 5 min at 80° C. and purified by successive elution with water on a C$_{18}$ Bond-Elut cartridge, lyophilised and derived for GC-EI-MS analysis.

Feeding Experiments

Four day old tobacco BY2 cells were incubated in BY2 medium for two days at 37° C. with Neu5Ac 10 mM or ManNAc 30 mM to assay Neu5Ac lyase or synthase activity in vivo respectively. After 2 d, BY2 cells were washed with BY2 medium without Neu5Ac or ManNAc and harvested. The cells were heated at 70° C. for 15 min in 70% ethanol to inactivate enzymes and then ground in a potter homogenizer. The homogenate was washed two times with 70% ethanol at 70° C. The remaining pellet and the supernatant were considered as representatives of the cell walls and the cytosolic free monosaccharides respectively. Monosaccharides of the supernatant fraction were then analysed by gas chromatography GC Analysis For the enzymatic assays, the reaction mixtures were first submitted to a purification step on C18 Seppack cartridges. The monosaccharides were eluted in 100% water. After lyophilisation, the samples were submitted to a 16 h methanolysis at 80° C. with dry 500 µL of 2 M methanolic-HCl. After evaporation of the methanol, the samples were re-acetylated by addition of 204 of anhydrous acetic anhydride and 20 µL of pyridine. The resulting N-acetyl methyl glycosides (methyl ester) were dried and then converted into their TMS-derivatives and separated by gas chromatography (GC). The gas chromatograph was equipped with a flame ionization detector, a WCOT fused silica capillary column (length 25 m, i.d. 0.25 mm) with CP-Sil 5 CP as stationary phase and helium as gas vector. The oven temperature program was: 2 min at 120° C., 10° C./min to 160° C., and 1.5° C./min to 220° C. and then 20° C./min to 280° C. The quantification of sugar was done by integration of peaks and determination of the corresponding molar values using response factors established with standard monosaccharides.

Transient Expression in Plants

*Agrobacterium* Growth.

The *Agrobacterium* clones containing a binary vector bearing the desired DNA constructs described above were grown for 24 hours at 28° C. in 2 mL of YEB or LB medium containing 25 and 50 µg/mL of carbenicillin and kanamycin, respectively. 10 µL of these cultures were used as starting inoculums to generate cultures of 25 mL of YEB induction medium (YEB medium, 10 mM 2 (N morpholino) ethanesulfonic acid (MES), pH adjusted to 5.6, 25 mg/L carbenicillin, 50 mg/L kanamycin, 20 µM acetosyringone). The latter were grown in rotary shaker (220 rpm) incubator at 28° C. for 18 hours or until an optical density at 600 nm (OD600) of 0.8 to 1 was reached.

Growth of Non-Transgenic Tobacco.

*Nicotiana benthamiana* and *Nicotiana tabacum* plants were grown from seeds in a peat-based substrate (AgroMix) in a greenhouse. Seedlings were initially raised in a nursery and later transplanted to pots. Plants were irrigated twice a day and receive 180 ppm of nitrogen at each application. Greenhouse condition were kept at 25° C. during the day and 21° C. during the night, under a long day photoperiod regime (16 h light/8 h dark cycles), with artificial lightning of 20 Watt $m^{-2}$ at plant level. Plants can be used at different growth stage, but were preferentially selected between 5 to 8 weeks of growth.

Transient Expression of Constructs in Tobacco.

Two transient expression methods were used in the present invention: Agro-inoculation or Agro-infiltration. In both methods, a mixture of two or three Agrobacteria cultures bearing the transfer-DNA (t-DNA) of interest are forced to enter into the intercellular spaces of the leaves. Once the physical barrier of the epidermis is crossed, the Agrobacteria infect neighbouring cells transferring t-DNA copies into the plant cells. With these methods, passage oft-DNA inside the nucleus is transient, the genes present on the t-DNA are episomally transcribed and the mRNA translated, leading to the production of the protein of interest in infected cells. The Agro-inoculation technique uses pressure applied with a syringe to insert the Agrobacteria mixture within the plant tissue, whereas the Agro-infiltration uses a controlled vacuum.

The *Agrobacterium* culture prepared as described earlier was centrifuged 8 min at 10 000 g, resuspended in the same volume of inoculation medium (10 mM MgCl2, 10 mM MES, adjusted to pH 5.6, and supplemented with 100 µM acetosyringone) and kept at room temperature (RT, 23° C.) for 1 h prior to inoculation. Alternatively, the suspension can be kept at 4° C. for 24 hours prior to inoculation. Transient transformation of *N. benthamiana* and *N. tabacum* were essentially performed as described in Liu and Lomonossoff (2002, Journal of Virological Methods, 105:343-348), with the following modifications. For the expression of the constructs described above, a mixture of two Agrobacteria strains was inoculated. The first strain contained one of the clones described above and the second strain contained the HcPro suppressor of silencing from the Potato Virus Y under the control of the 35S promoter. After inoculation, the plants were incubated in a greenhouse. Temperature was kept at a minimum 23° C. during the day and 21° C. during the night. Plants were irrigated twice a day and received 180 ppm of nitrogen at each application. Harvest of biomass was undertaken after 4-8 days.

Preparation of Soluble Protein Extracts from Transformed Biomass.

Leaves were analyzed directly after harvesting or after freezing the biomass at −80° C. A biomass of Agro-inoculated or Agro-infiltrated leaves of ~0.1-1 g was weighted and used to generate a total protein liquid extract.

Several extraction methods were used to generate total protein extracts: by grounding the vegetable tissue with a mortar and a pestle, by using a polytron, or by pulverizing it in a MixerMill300 (MM300) from Retsch. 0.1-1 g of plant biomass was transferred into a clean and pre-cooled mortar. Cold extraction buffer (Tris 50 mM, NaCl 150 mM pH 7.4 buffer containing, 2 mM $CaCl_2$ and 4% butanol) was added at a 1:3 ration (w/v) as well as PMSF and chymostatin to final concentrations of 1 mM and 10 µM, respectively. Leaves were ground with a pestle until a homogeneous preparation was obtained. The plant extract was then transferred into a 1.5 mL microtube and centrifuged at 20,000 g for 20 min at 4° C. Alternatively, 0.1 g of plant tissue with 0.3 mL of extraction buffer was introduced into non-sterile 1.5 microtube. A tungsten bead was added to each tube. The box was submitted to 3 min cycle of agitation at 30 Hz. The cycle was repeated 2 times. The plant extracts were then centrifuged as described above. Alternatively, 1 g of biomass was pulverized with 3 mL of extraction buffer using a polytron.

Following centrifugation, the supernatant was transferred into a clean microtube and maintained on ice. Finally, the total protein content of individual protein extracts was measured by the Bradford method using BSA as the reference protein.

Example 1

Expression of the *E. coli* Neu5Ac Lyase in Tobacco BY2 Cells

The gene encoding Neu5Ac lyase from *Escherichia coli* K1 (accession number: D00067) was introduced into tobacco BY2 cells. Transgenic BY2 calli were generated after *Agrobacterium* mediated transformation with the plasmid pBLTI121 containing the *E. coli* K1 Neu5Ac lyase gene. Another construct was tagged at its C-terminus with a FLAG epitope to allow immunodetection of the recombinant protein in transformants. The transformants selected for kanamicin resistance were analysed for mRNA levels by RT-PCR. Thirty-six from 48 transformants expressing the Neu5Ac lyase transcript and 30 from 50 transformants expressing the Neu5Ac lyase-FLAG transcript were obtained. Calli harbouring the highest mRNA expression levels were transferred in suspension cultures for the characterisation of Neu5Ac lyase activity. The presence of the Neu5Ac lyase-FLAG was determined in protein cytosolic extracts of transformed BY2 cells by western-blot analysis. A single protein band with an apparent MW of 32 kDa was specifically immunodetected in the transformed cells using anti-FLAG antibodies (FIG. 1a).

Enzymatic assays were carried out on soluble protein extracts from suspension-cultured BY2 cells expressing the Neu5Ac lyase and Neu5Ac lyase-FLAG. Both extracts showed a lyase activity. Further analysis was conducted on protein extracts isolated from cells expressing the non-tagged lyase. These extracts were first incubated in the presence of Neu5Ac to investigate their lyase activity. FIGS. 1b and 1c show the GC profiles of the end-products formed by incubating a Neu5Ac lyase protein extract in absence (FIG. 1b) or presence of Neu5Ac (FIG. 1c) at pH 7 and at 37° C. Three signals (peak 1, is a shoulder of an endogenous signal) were clearly detected when the extract was incubated with Neu5Ac. These signals eluted at retention times similar to those of pyranose (peak 1) and furanose (peaks 2 and 3) forms of standard ManNAc. Gas chromatography coupled to Electron Impact Mass Spectrometry (GC-EI MS) of the sample confirmed the assignment of these signals to 1-O-methyl persilyl derivatives of ManNAcp (FIG. 1e) and ManNAcf (FIG. 1f). Diagnostic ions at m/z=173 and 186 were assigned to fragments containing the nitrogen atom, as usually observed for aminosugars.

Incubation of a cytosolic protein extract from wild-type tobacco BY2 cells with Neu5Ac in similar conditions did not result in any formation of ManNAc (data not shown), thus demonstrating the absence of an endogenous lyase activity in plants. This data indicates that BY2 cells transformed with the *E. coli* Neu5Ac lyase gene expressed a functional enzyme able to cleave Neu5Ac into D-ManNAc.

The optimum pH of the recombinant enzyme was determined to be about 7, based upon GC quantification of D-ManNAc generated in assays carried out in a 4-10 pH range (data not shown). Furthermore, the recombinant enzyme exhibited a temperature dependent activity with high lyase activity observed in a 25-37° C. range. At pH 7 and at 37° C., a soluble protein extract from transformed cells formed 0.5 µmole of ManNAc from 10 µmoles of Neu5Ac, in 1 h. Below 15° C., only residual activity was detected.

Figure 2:
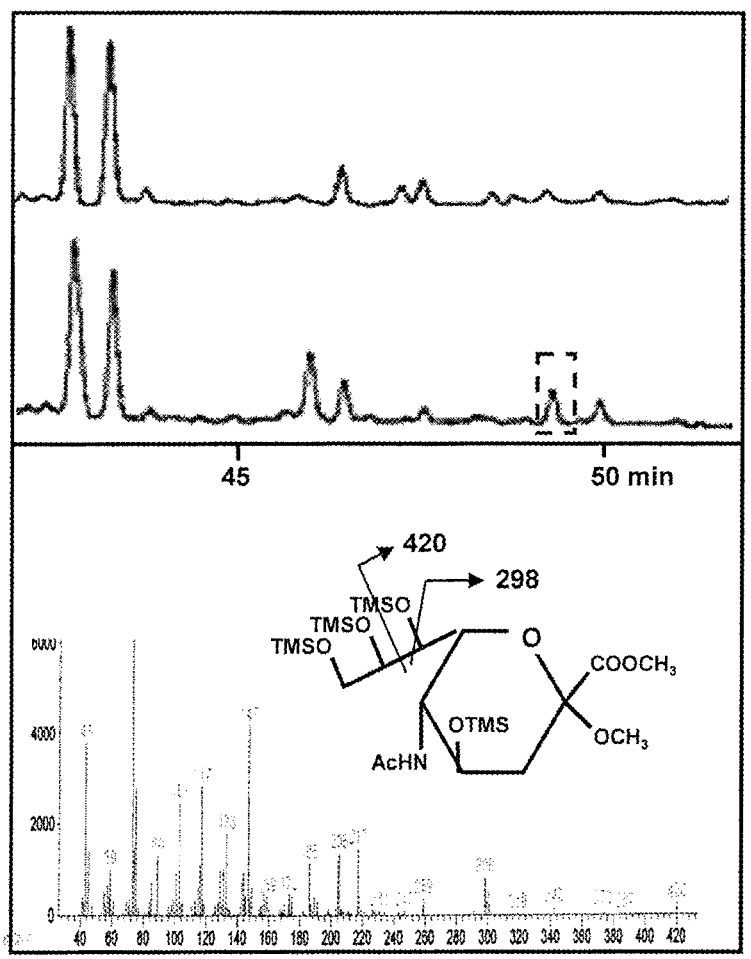
FIG. 2a and FIG. 2b show Gas chromatography profiles of the end-products obtained after incubation at pH 7 and 37° C. of cytosolic proteins, isolated from tobacco BY2 cells expressing the Neu5Ac lyase, without (FIG. 2a) or with (FIG. 2b) D-ManNAc and pyruvate.
FIG. 2c shows Electron impact mass spectrum of the peak appearing in profile (FIG. 2b). Main fragment ions of 1-O-methyl methylester persilyl derivatives of N-acetylneuraminic acid are indicated.

The ability of the recombinant Neu5Ac lyase to synthesise Neu5Ac was determined by incubating protein extracts of transformed tobacco BY2 cells with D-ManNAc and pyruvate at pH 7 and 37° C. FIGS. 2a and 2b show the GC profiles of end-products after incubation in the absence or presence of substrates respectively. When compared to the control profile (FIG. 2a), GC profile of the reaction conducted in the presence of D-ManNAc and pyruvate showed a signal at a retention time expected for Neu5Ac (box in FIG. 2b). The electron impact mass spectrum (EI MS) of this signal (FIG. 2c), exhibited the diagnostic ions at m/z=298 and 420 specific for Neu5Ac fragmentation, as well as the ion at m/z=186 assigned to the nitrogen-containing fragment. This data indicates that the recombinant lyase is able to synthesise Neu5Ac in presence of D-ManNAc and pyruvate.

In planta activity of the Neu5Ac lyase was determined by feeding tobacco BY2 cells with 10 mM Neu5Ac. The toxicity of Neu5Ac on tobacco BY2 cells were investigated, and no toxic effects were observed over a 48 h period by testing the cell viability using propidium iodide and fluorescein diacetate. The formation of D-ManNAc was determined by analysing cytosolic monosaccharides by GC after a 48 h period at temperature ranging from 23° C. to 37° C. D-ManNAc was detected in all treatments (FIG. 1d). The quantification of D-ManNAc by GC showed a 25-fold increase in the content of this aminosugar at 37° C. compared to 23° C. These in vivo experiments demonstrate that the Neu5Ac lyase is biologically active in planta and is able to act upon an exogenously supplied substrate.

Expression of *Campylobacter jejuni* NeuB2 in Tobacco BY2 and Alfalfa Plants

Figure 3:
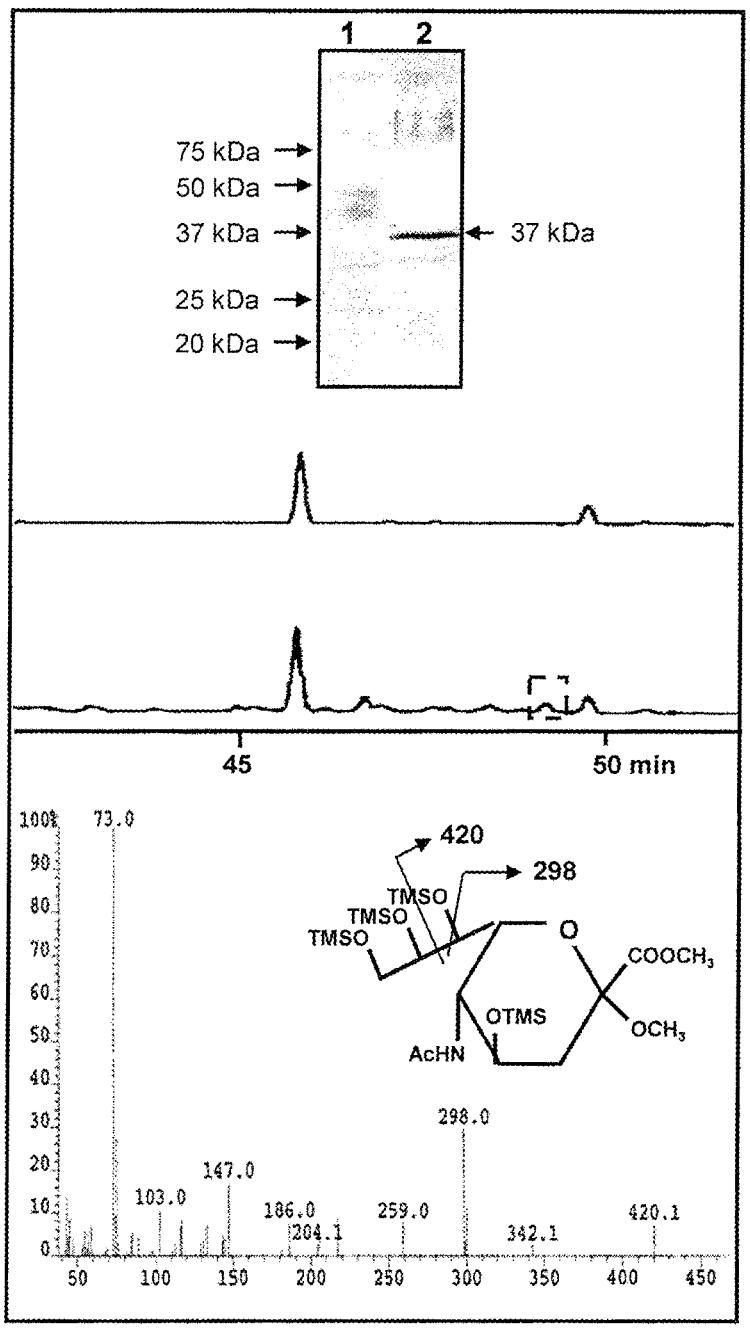
FIG. 3a shows a Western-blot analysis of cytosolic proteins extracted from wild-type (line 1) or transgenic tobacco BY2 cells expressing the NeuB2-FLAG (line 2) using anti-FLAG antibodies.
FIG. 3b and FIG. 3c show Gas chromatography profiles of the end-products obtained after incubation at pH 8 and 37° C. of soluble proteins, extracted from leaves of alfalfa plants expressing the NeuB2, without (FIG. 3b) or (FIG. 3c) D-ManNAc and PEP.
FIG. 3d shows an Electron impact mass spectrum of the peak appearing in profile (FIG. 3c). Main fragment ions of 1-O-methyl methylester persilyl derivatives of N-acetylneuraminic acid are indicated.

Neu5Ac synthase, NeuB2, from *Campylobacter jejuni* (accession number: NC002163) catalyzes the formation of Neu5Ac by condensation of D-ManNAc and PEP. Transgenic BY2 calli were generated after *Agrobacterium* mediated transformation with the plasmid pBLTI121 containing the neuB2 cDNA. For immunodetection of the protein, a second construct was tagged at its C-terminus end with a FLAG epitope. The transformants selected for kanamicin resistance were analysed for mRNA levels by RT-PCR. Calli harbouring the highest mRNA expression levels were transferred in suspension cultures for analysis. The accumulation of NeuB in transformed BY2 cells was then determined by western-blot analysis of a protein soluble extract isolated from BY2 cells transformed with the NeuB2-FLAG sequence. As illustrated in FIG. 3a, anti-FLAG antibodies specifically recognised a single protein band at MW-37 kDa consistent with the expected molecular weight of the synthase. neuB2 was also introduced in alfalfa plants by *Agrobacterium*-mediated transformation and in vitro regeneration of plants (Tian et al., 2002). From 34 transformed plants, 29 were demonstrated to express the neuB2 transcript.

Prior to the analysis of transformed cells and plants expressing the bacterial Neu5Ac synthase, the occurrence of endogenous Neu5Ac synthase activity was investigated. Protein soluble extracts from both wild-type tobacco BY2 cells and alfalfa plants were incubated with D-ManNAc and PEP. The monosaccharides formed in the assays were separated by GC and characterised by GC-EI MS. No peak or EI MS diagnostic ions assigned to Neu5Ac were detected, indicating that plants do not express endogenous enzymes able to form Neu5Ac by condensation of PEP onto D-ManNAc.

The synthase activity of the recombinant NeuB2 expressed in plants was determined by incubation of D-ManNAc and PEP with soluble protein extracts isolated from tobacco BY2 cells or alfalfa plants transformed with neuB2 gene. FIGS. 3b and 3c show the GC profiles obtained by incubation of a transformed alfalfa extract without (FIG. 3b) or with (FIG. 3c) D-ManNAc and PEP at pH=8 and 37°

C. A peak eluted at the expected retention times for Neu5Ac was specifically detected after incubation with the substrates of the synthase. EI MS of this peak exhibited a fragmentation pattern similar to the one of a standard Neu5Ac, with diagnostic ions at m/z=298 and 420. Those ions were not detected in the EI-MS spectrum of the corresponding region of the GC profile after incubation in absence of D-ManNAc (FIG. 3b).

The same result was obtained by the analysis of tobacco BY2 cells expressing the NeuB2 or the NeuB2-FLAG sequence.

Therefore, expression of neuB2 in both tobacco BY2 cells and alfalfa plants results in the production of a functional Neu5Ac synthase.

REFERENCES

Angatta, T. and Varki, A. (2002) Chemical diversity in the sialic acids and related a-keto acids: an evolutionary perspective. *Chem Rev.*, 102, 439-469.

Bakker, H., Bardor, M., Molhoff, J., Gomord, V., Elbers, I., Stevens, L., Jordi, W., Lommen, A., Faye, L., Lerouge, P. and Bosch D. (2001) Humanized glycans on antibodies produced by transgenic plants. *Proc. Natl. Acad. Sci. USA*, 98, 2899-2904.

Bardor M, Faveeuw C, Fitchette A-C, Gilbert D, Galas L, Trottein F, Faye L and Lerouge P. (2003) Immureactivity in mammals of two typical plant glyco-epitopes, core-alpha(1,3)-fucose and core-xylose. *Glycobiology*, 13, 427-434.

Bravo, I. G., Garcia-Vallvé, S., Romeu, A. and Reglero, A. (2004) Prokaryotic origin of cytidyltransferases and □-ketoacid synthases. *Trends in Microbiol.*, 12, 120-128.

Busse, U., Levée, V., Trépanier, S. and Vézina, L. (2001) Production of antibodies in alfalfa (*Medicage sativa*). In: *Molecular Farming of plants and animal for human and veterinary medicine.* (Erickson, L., ed), pp 199-219. J. Wiley and sons, New York.

Delmas F, Petit J, Joubes J, Séveno M, Paccalet T, Hernould M, Lerouge P, Mouras A and Chevalier C. (2003) The gene expression and enzyme activity of plant 3-deoxy-D-manno-2-octulosonic acid-8-phosphate synthase are preferentially associated with cell division in a cell cycle-dependent manner. *Plant Physiol.*, 133, 348-360.

Gomord, V., Fitchette-Lainé, A.-C., Denmat, L.-A., Michaud, D., and Faye, L. (1998) Production of foreign proteins in tobacco cell suspension culture. In Methods in Biotechnology, C. C. Cunningham and A. J. R. Porter, eds. Totowa, N.J., Humana Press, pp. 155-164.

Hofgen, R. and Willmitzer L. (1988) Storage of competent cells for *Agrobacterium* transformation. *Nucleic Acids Res* 16, 9877.

Kelm, S. And Schauer, R. (1997) Sialic acids in molecular and cellular interactions. *Int. Rev. Cytol.* 175, 137-240.

Ko, K., Tekoah, Y., Rudd, P. M., Harvey, D. J., Dwek, R. A., Spitsin, S., Hanlon, C. A., Rupprecht C., Dietzschold, B., Golovkin, M. and Koprowski, H. (2003) Function and glycosylation of plant-derived antiviral monoclonal antibody. *Proc. Natl Acad. Sci. USA*, 101, 8013-8018

Lerouge, P., Cabanes-Macheteau, M., Rayon, C., Fitchette-Lainé, A.-C., Gomord, V. and Faye, L. (1998) N-glycoprotein biosynthesis: recent development and future trends. *Plant Mol. Biol.*, 38, 31-48.

Maru, I., Ohnishi, J., Ohta, Y. and Tsukada, Y. (1998) Simple and large-scale production of N-acetylneuraminic acid from N-acetyl-D-glucosamine and pyruvate using N-acyl-D-glucosamine epimerase and N-acetylneuraminate layse. *Carbohydr. Res.*, 306, 575-578.

Matsumoto, S., Ikura, K., Ueda, M. and Sasaki, R. (1995) Characterization of a human glycoprotein (erythropoietin) produced in cultured tobacco cells. *Plant Mol. Biol.* 27, 1163-1172.

Misaki, R., Fujiyama, K., and Seki, T, (2006) Expression of human CMP-N-acetyneuraminic acid synthetase and CMP-sialic acid transporter in tobacco suspension-cultured cell. *Biochem. Biophys. Res. Comm.* 339, 1184-1189.

Murashige, T. and Skoog, F. (1962) A revised medium for rapid growth and bioassays with tobacco tissue cultures. *Physiol. Plant.* 15, 473.

Pagny, S., M. Cabanes-Macheteau, J. W. Gillikin, N. Leborgne-Castel, P. Lerouge, R. S. Boston, L. Faye and V. Gomord (2000). Protein recycling from the Golgi apparatus to the endoplasmic reticulum in plants and its minor contribution to calreticulin retention. *Plant Cell* 12, 739-756.

Palacpac, N. Q., Yoshida, S., Sakai, H., Kimura, Y., Fujiyama, K., Yoshida, T. and Seki, T. (1999) Stable expression of human beta 1,4-galactosyltransferase in plant cells modifies N-linked glycosylation patterns. *Proc. Natl. Acad. Sci. USA* 96, 4692-4697.

Ray, P. H. (1980) Purification and characterization of 3-deoxy-D-manno-octulosonic 8-phosphate synthase from *Escherichia coli. J. Bacteriol.* 141, 635-644.

Sriraman, R., Bardor, M., Sack, M., Vaquero, C., Faye, L., Fischer, R., Finnern, R. and Lerouge, P. (2004) Recombinant anti-hCG antibodies retained in the endoplasmic reticulum of transformed plants lack core xylose and core □(1,3)-fucose residues. Plant Biotech. J., 2, 279-287.

Séveno, M., Bardor, M., Paccalet, T., Gomord, V., Lerouge, P. and Faye, L. (2004) Glycoprotein sialylation in plants? *Nature Biotech.*, 22, 5-6.

Strohmaier, H., Remler, P., Renner, W. and Högenauer, G. (1995) Expression of genes kdsA and kdsB involved in 3-deoxy-D-manno-octulosonic acid metabolism and biosynthesis of enterobacterial lipopolysaccharide is growth phase regulated primary at the transcriptional level in *Escherichia coli* K-12. *J. Bacteriol.* 177, 4488-4500.

Tian, L., Wang, H., Wu, K, Latoszek-Green, M., Hu, M., Miki, B., Brown, D. C. W. (2002) Efficient recovery of transgenic plants through organogenesis and embryogenesis using cryptic promoter to drive marker gene expression. *Plant Cell Rep.*, 20, 1181-1187.

Triguero, A., Cabrera, G., Cremata, J., Yuen, C-T., Wheeler J. and Ramirez N. I. (2005) Plant-derived mouse IgG monoclonal antibody fused to KDEL endoplasmic reticulum-retention signal is N-glycosylated homogeneously throughout the plant with mostly high-mannose-type N-glycans. *Plant Biotech. J.* 3, 449-457

Tanner, M. E. (2005) The enzymes of sialic acid biosynthesis. *Bioorg. Chem.*, 33, 216-228.

Wee, E. Q., Sherrier, D. J., Prime, T. A. and Dupree, P. (1998) Targeting of active sialyltransferase to the plant Golgi apparatus. *Plant Cell*, 10, 1759-1768.

All citations are hereby incorporated by reference.

The present invention has been described with regard to one or more embodiments. However, it will be apparent to persons skilled in the art that a number of variations and modifications can be made without departing from the scope of the invention as defined in the claims.

What is claimed is:

1. A method of synthesizing sialic acid comprising,
   i) providing a transgenic plant comprising a nucleotide sequence encoding bacterial N-acetyl neuraminic acids lyase utilizing N-acetyl-D-mannosamine as a substrate, the nucleotide sequence operatively linked with a regulatory region that is active in the plant, and
   ii) growing the transgenic plant and expressing the nucleotide sequence thereby synthesizing sialic acid; and
   iii) recovering free sialic acid from the transgenic plant.

2. A method of synthesizing sialic acid comprising,
   i) providing a transgenic plant cell comprising a nucleotide sequence encoding bacterial N-acetyl neuraminic acid lyase utilizing N-acetyl-D-mannosamine as a substrate, the nucleotide sequence operatively linked with a regulatory region that is active in the plant, and
   ii) growing the transgenic plant cell and expressing the nucleotide sequence thereby synthesizing sialic acid; and
   iii) recovering free N-acetyl neuraminic acid (Neu5Ac) from the transgenic plant cell.

3. The method of claim 1, wherein the regulatory region is selected from the group consisting of a constitutive promoter, an inducible promoter, a tissue specific promoter, and a developmental promoter.

* * * * *

SEQUENCE LISTING

<160> NUMBER OF SEQ ID NOS: 9

<210> SEQ ID NO 1
<211> LENGTH: 8
<212> TYPE: PRT
<213> ORGANISM: Artificial Sequence
<220> FEATURE:
<223> OTHER INFORMATION: synthetic FLAG sequence polypeptide

<400> SEQUENCE: 1

Asp Tyr Lys Asp Asp Asp Asp Lys
1               5

<210> SEQ ID NO 2
<211> LENGTH: 36
<212> TYPE: DNA
<213> ORGANISM: Artificial Sequence
<220> FEATURE:
<223> OTHER INFORMATION: Lyase-FLAG-P1

<400> SEQUENCE: 2
cggggtacca gagagatggc aacgaattta cgtggc                                36

<210> SEQ ID NO 3
<211> LENGTH: 60
<212> TYPE: DNA
<213> ORGANISM: Artificial Sequence
<220> FEATURE:
<223> OTHER INFORMATION: Lyase-FLAG-P2

<400> SEQUENCE: 3
gccgagctct cacttgtcat cgtcatcctt gtaatccatc ccgcgctctt gcatcaactg      60

<210> SEQ ID NO 4
<211> LENGTH: 38
<212> TYPE: DNA
<213> ORGANISM: Artificial Sequence
<220> FEATURE:
<223> OTHER INFORMATION: neuB2-FLAG-P1

<400> SEQUENCE: 4
cggggtacca gagagatgaa aaaactttta atcatcgc                              38

<210> SEQ ID NO 5
<211> LENGTH: 60
<212> TYPE: DNA
<213> ORGANISM: Artificial Sequence
<220> FEATURE:
<223> OTHER INFORMATION: neuB2-FLAG-P2

<400> SEQUENCE: 5
gccgagctct cacttgtcat cgtcatcctt gtaatccatc tcacggataa gctcatcttc      60

<210> SEQ ID NO 6
<211> LENGTH: 37
<212> TYPE: DNA
<213> ORGANISM: Artificial Sequence
<220> FEATURE:
<223> OTHER INFORMATION: Lyase-P1

<400> SEQUENCE: 6
aataggccat tacggccatg gcaacgaatt tacgtgg                               37

<210> SEQ ID NO 7
<211> LENGTH: 35
<212> TYPE: DNA

```
<213> ORGANISM: Artificial Sequence
<220> FEATURE:
<223> OTHER INFORMATION: Lyase-P2

<400> SEQUENCE: 7
aataggccga ggcggcctca cccgcgctct tgcat                               35

<210> SEQ ID NO 8
<211> LENGTH: 35
<212> TYPE: DNA
<213> ORGANISM: Artificial Sequence
<220> FEATURE:
<223> OTHER INFORMATION: neuB2-P1

<400> SEQUENCE: 8
aataggccat tacggccatg aaaaaaactt taatc                               35

<210> SEQ ID NO 9
<211> LENGTH: 35
<212> TYPE: DNA
<213> ORGANISM: Artificial Sequence
<220> FEATURE:
<223> OTHER INFORMATION: neuB2-P2

<400> SEQUENCE: 9
aataggccga ggcggcctta ctcacggata agctc                               35
```